United States Patent
Eggers

(10) Patent No.: US 8,475,444 B2
(45) Date of Patent: *Jul. 2, 2013

(54) HEATED HEMOSTATIC SURGICAL BLADE SYSTEM AND METHOD

(75) Inventor: Philip E. Eggers, Dublin, OH (US)

(73) Assignee: Hemostatix Medical Technologies, LLC, Bartlett, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,287

(22) Filed: Mar. 23, 2012

(65) Prior Publication Data

US 2012/0239027 A1    Sep. 20, 2012

Related U.S. Application Data

(62) Division of application No. 11/980,310, filed on Oct. 30, 2007, now Pat. No. 8,142,425.

(51) Int. Cl.
*A61B 18/04*    (2006.01)
*A61B 17/32*    (2006.01)

(52) U.S. Cl.
USPC .................. 606/29; 606/28; 606/31; 606/45

(58) Field of Classification Search
USPC .......................................... 606/27–31, 41–45
See application file for complete search history.

(56) References Cited

U.S. PATENT DOCUMENTS

| | | | | |
|---|---|---|---|---|
| 4,231,371 A * | 11/1980 | Lipp | ............................... | 606/31 |
| 4,485,810 A * | 12/1984 | Beard | .............................. | 606/28 |
| 4,491,558 A * | 1/1985 | Gardner | ........................... | 419/23 |
| 4,862,890 A * | 9/1989 | Stasz et al. | ...................... | 606/48 |
| 5,000,912 A * | 3/1991 | Bendel et al. | ................... | 420/34 |
| 5,308,311 A * | 5/1994 | Eggers et al. | ................... | 600/28 |
| 7,993,338 B2 * | 8/2011 | Klimovitch et al. | ........... | 606/42 |

* cited by examiner

*Primary Examiner* — Linda Dvorak
*Assistant Examiner* — Amanda Scott
(74) *Attorney, Agent, or Firm* — Jerry K. Mueller, Jr.; Mueller Law, LLC

(57) ABSTRACT

A hemostatic surgical blade is described which is formed of five symmetrically disposed layers. A martensitic stainless steel core is provided with oppositely disposed faces which are bonded to hard pure copper thermal transfer layers which, in turn, are supported by buttressing layers of austenitic stainless steel. The blade is heated by a blade heater circuit which is provided as a flexible circuit carrying one or more resistor heaters and associated leads supported by a polyimide substrate. A thermally conductive and electrically insulative adhesive is used to bond the flexible circuit to a blade blank. The system employs a multi-lead cable which is removable from an instrument handle. One blade embodiment involves an elongate stem for accessing body cavities and another embodiment incorporates a controller function within an instrument handle.

17 Claims, 21 Drawing Sheets

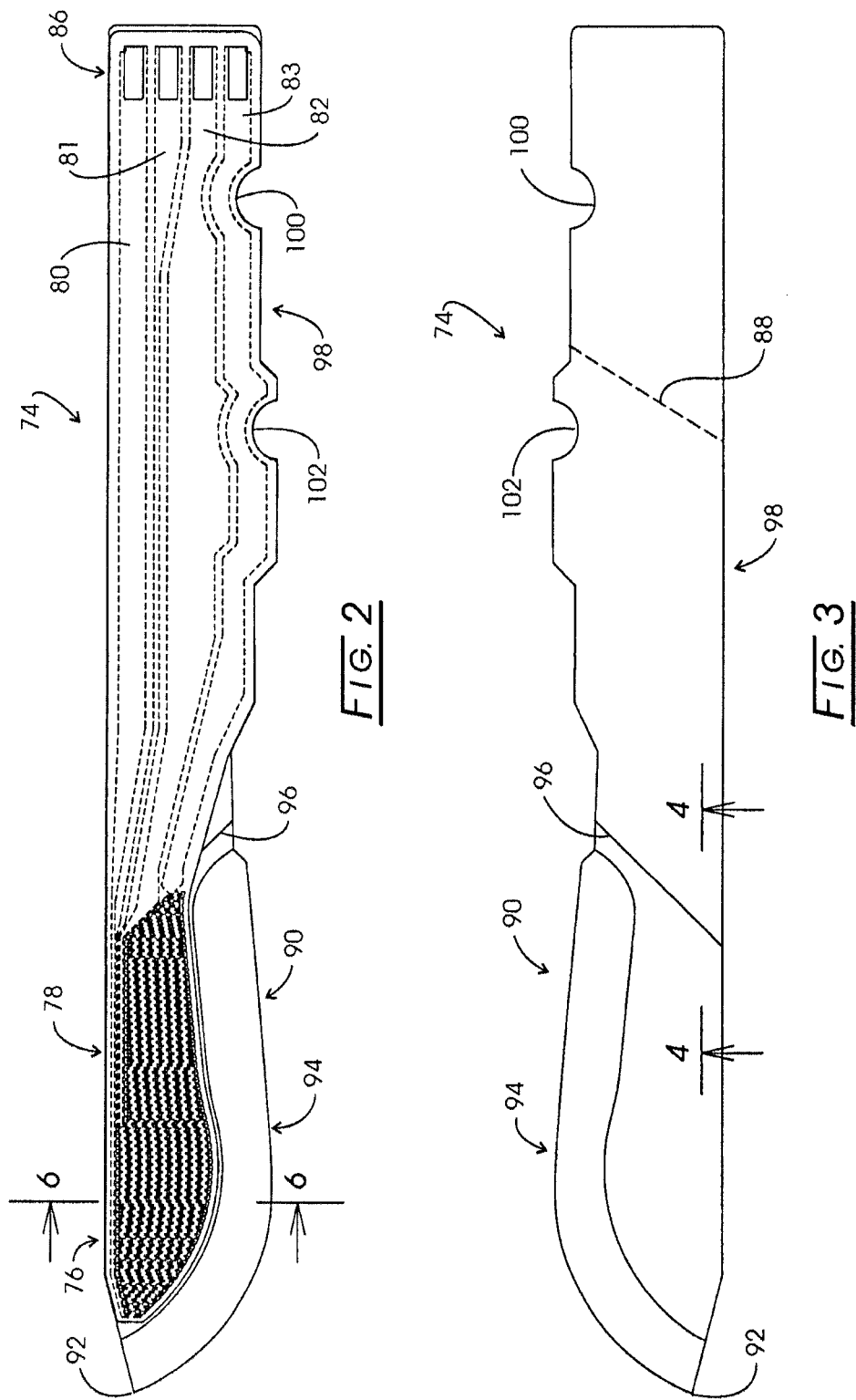

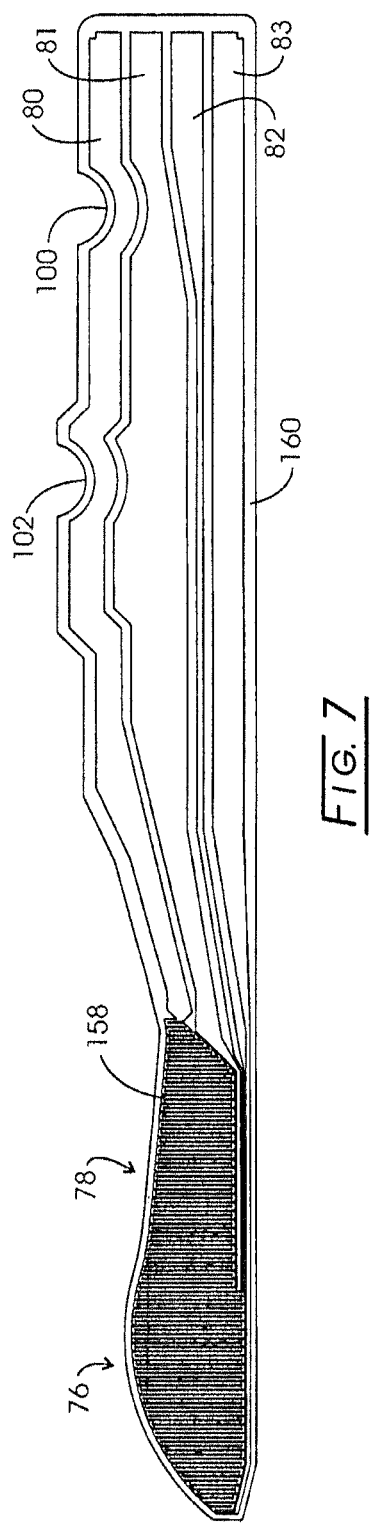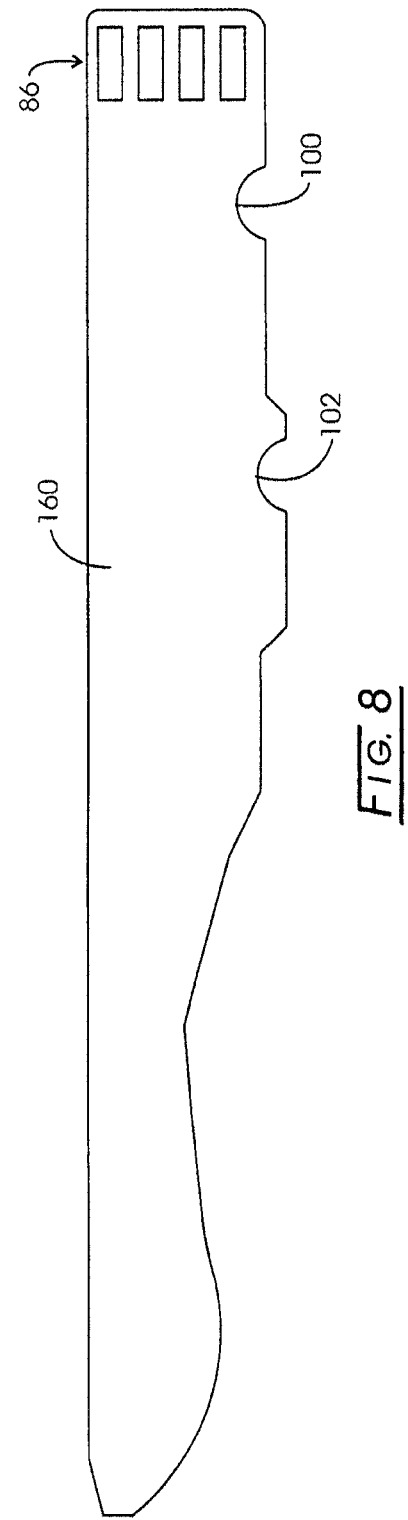

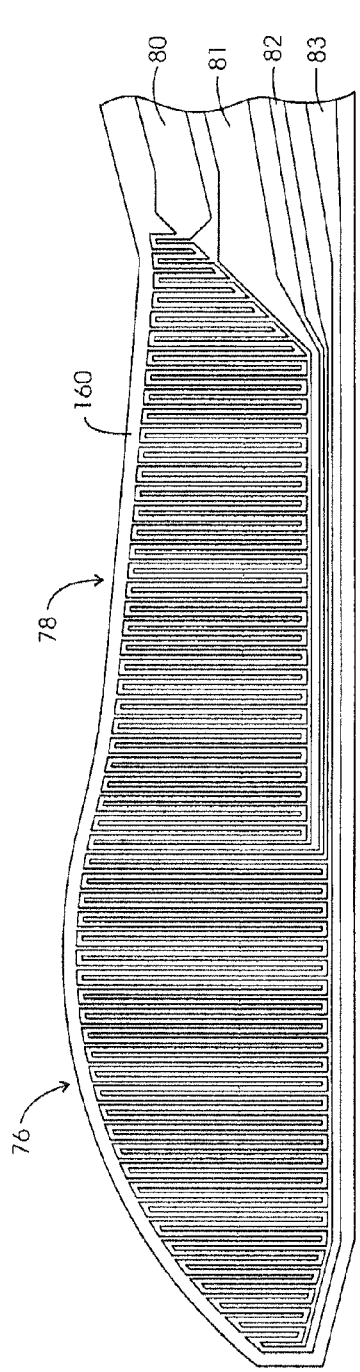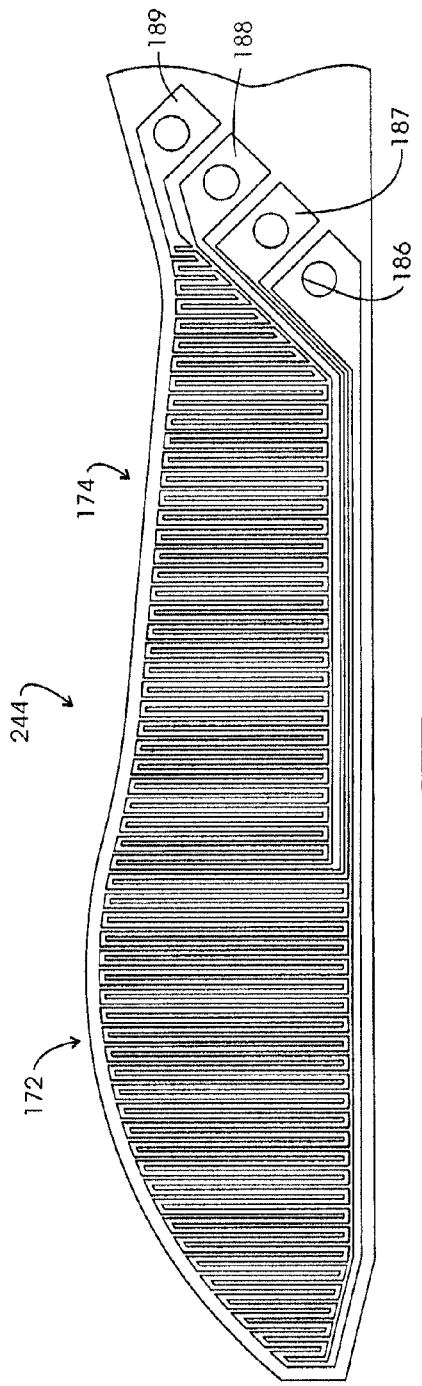

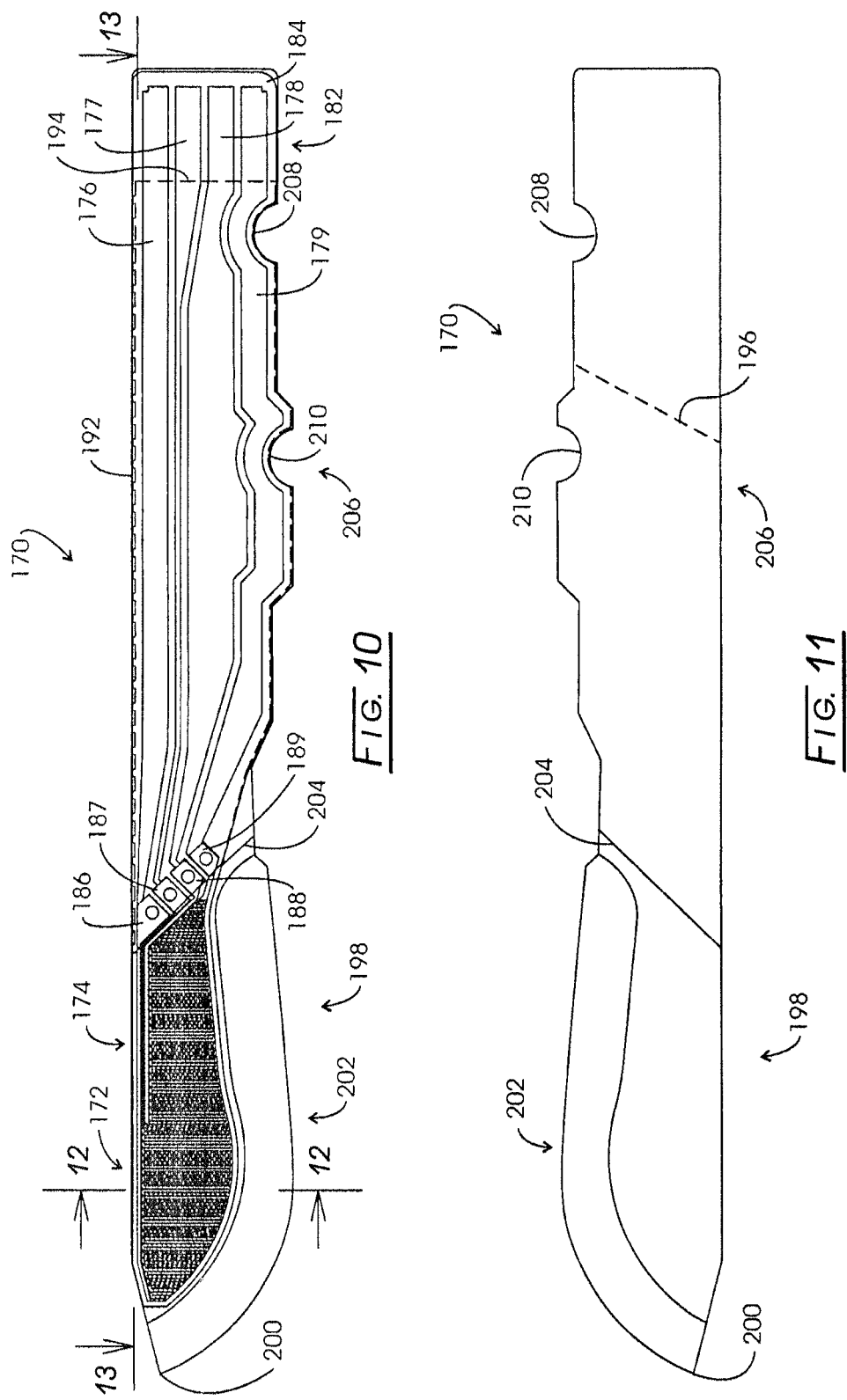

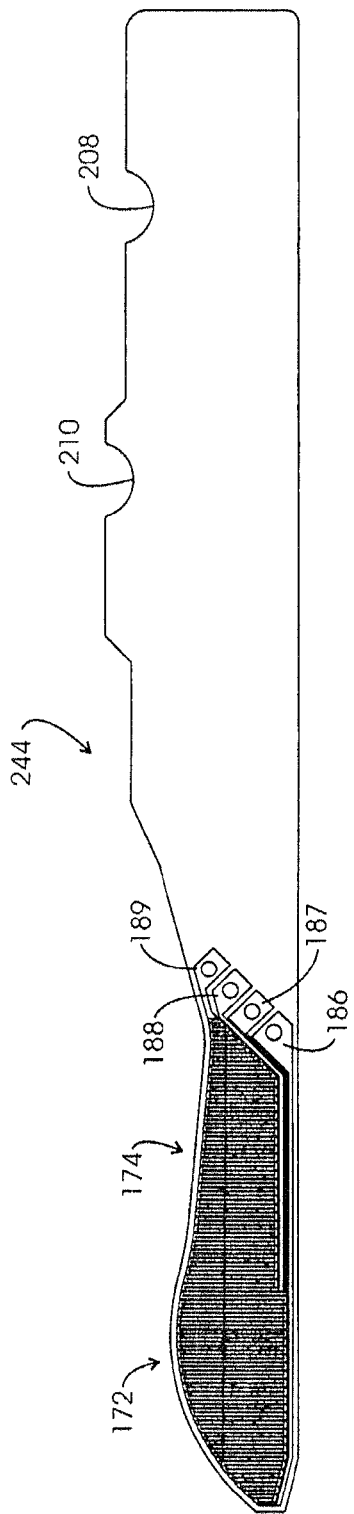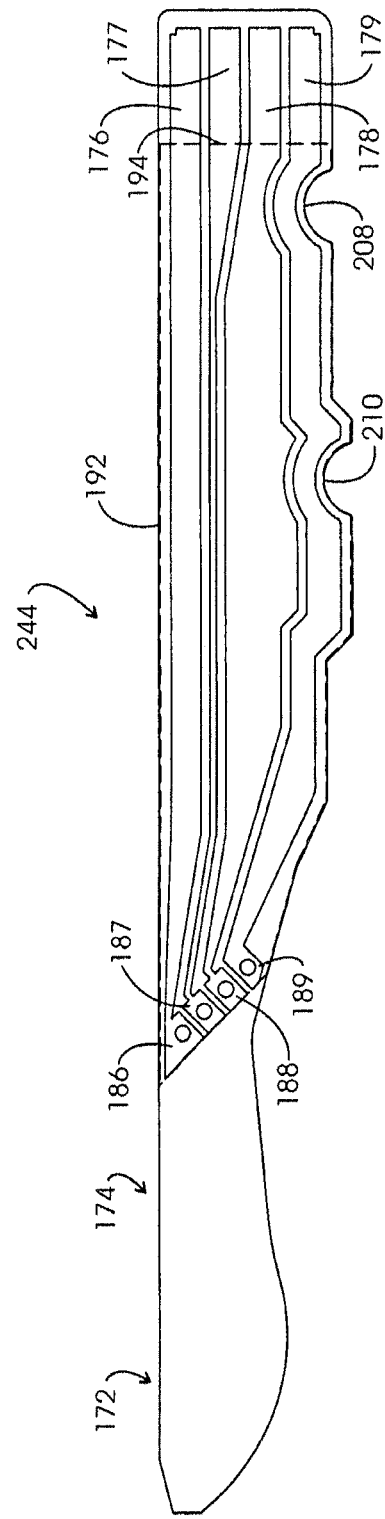

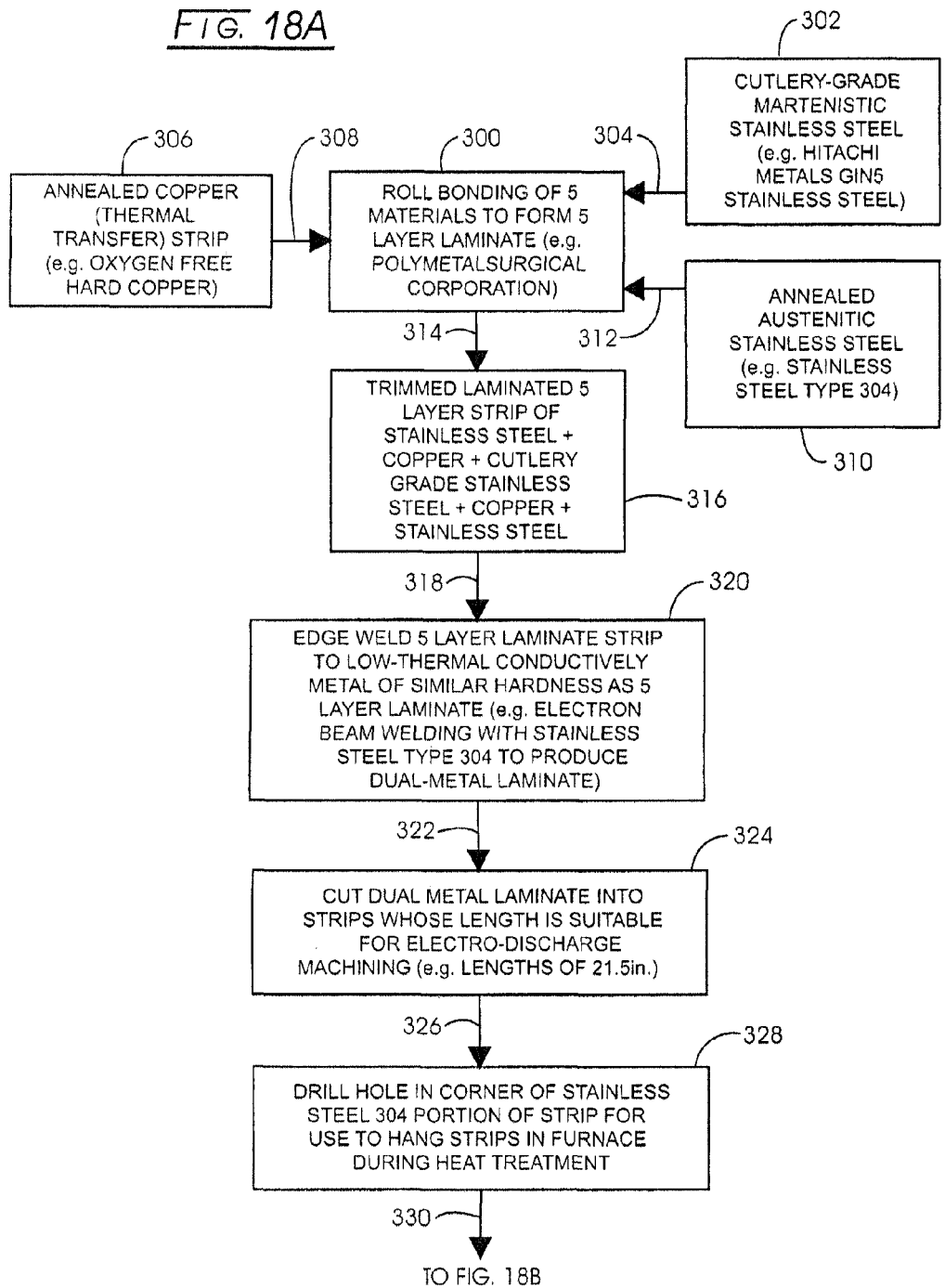

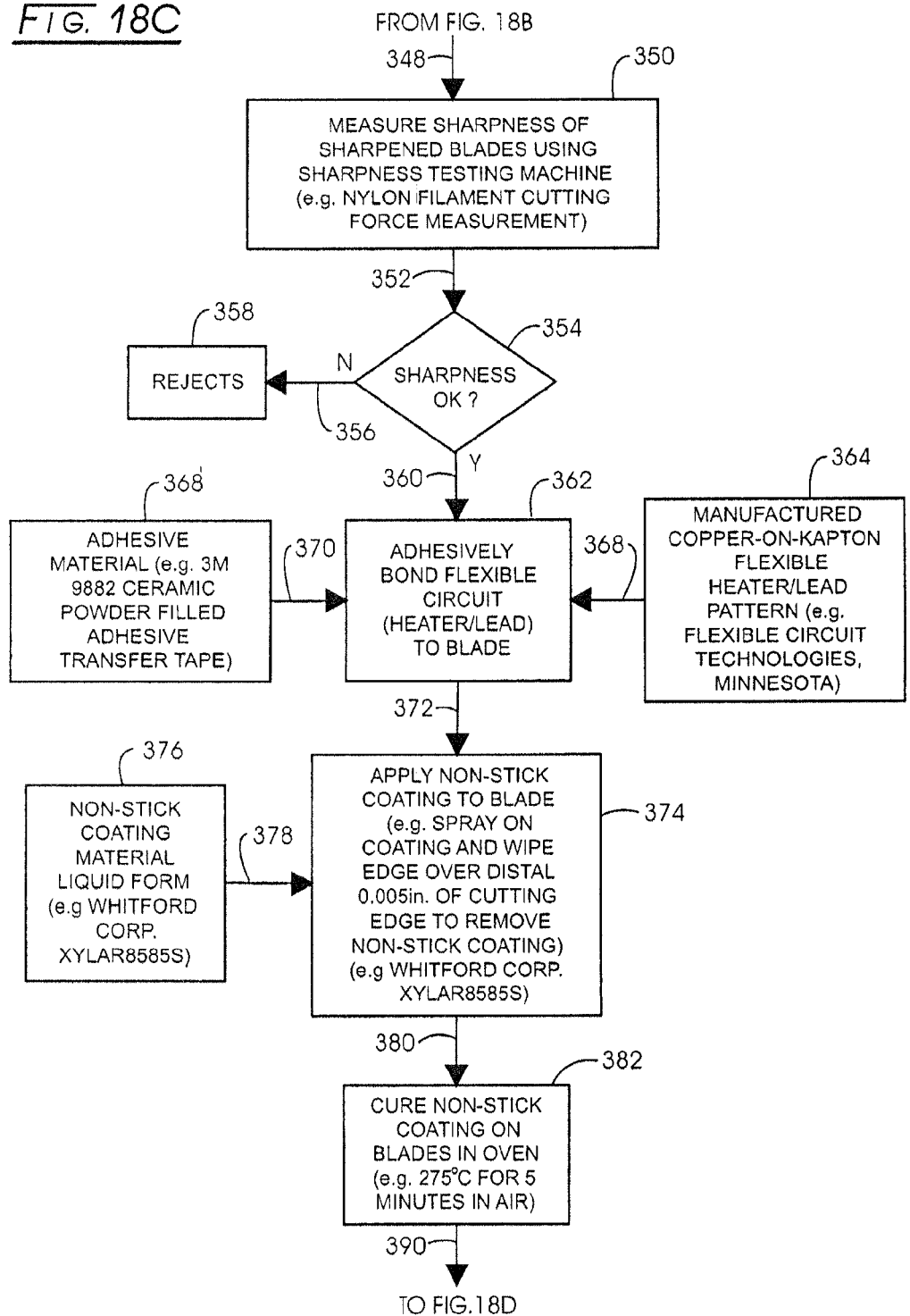

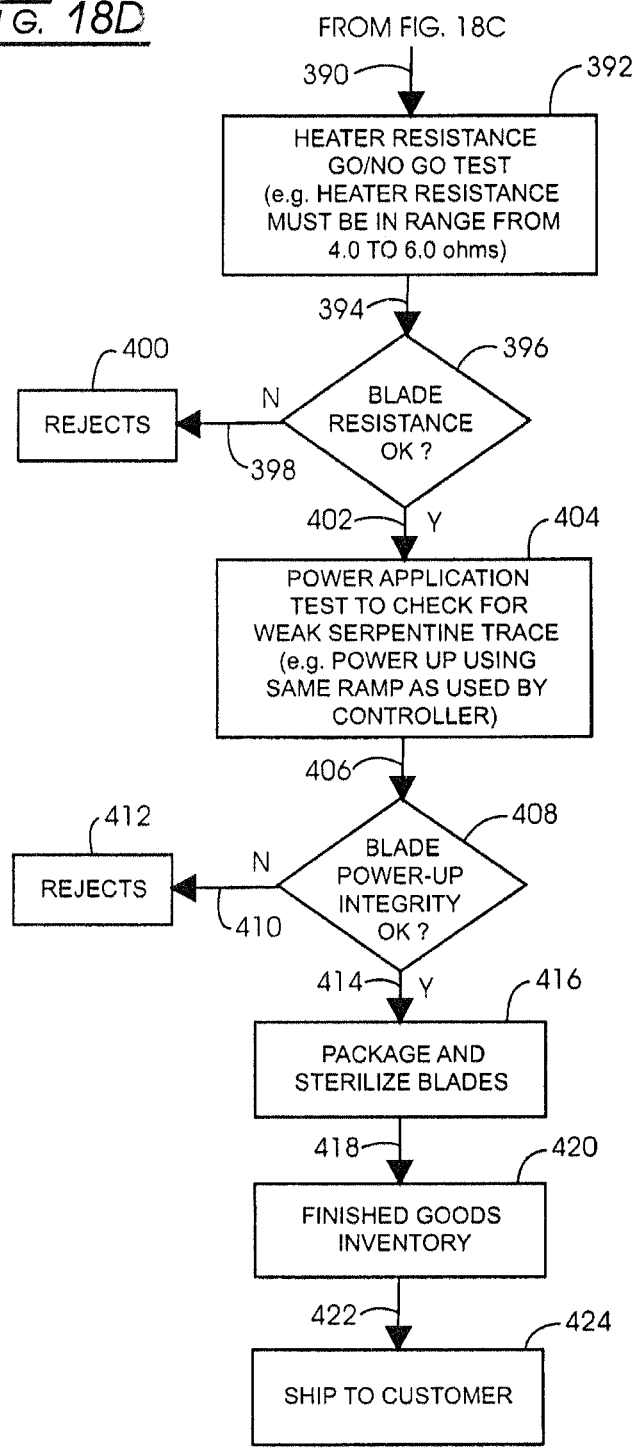

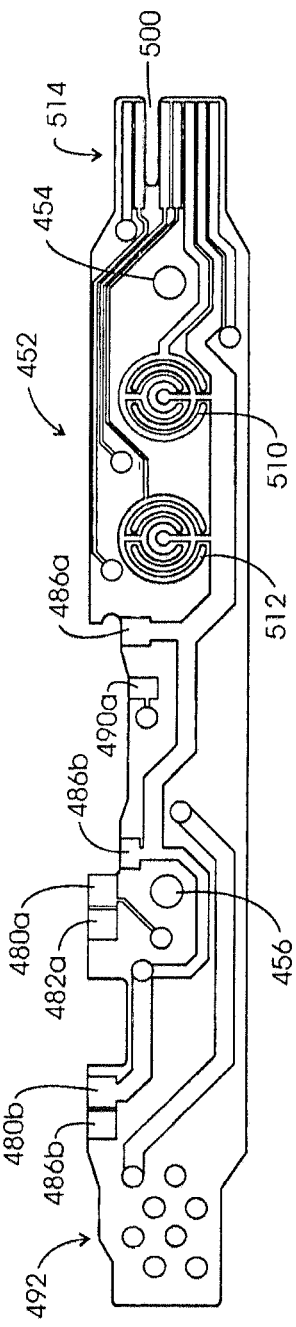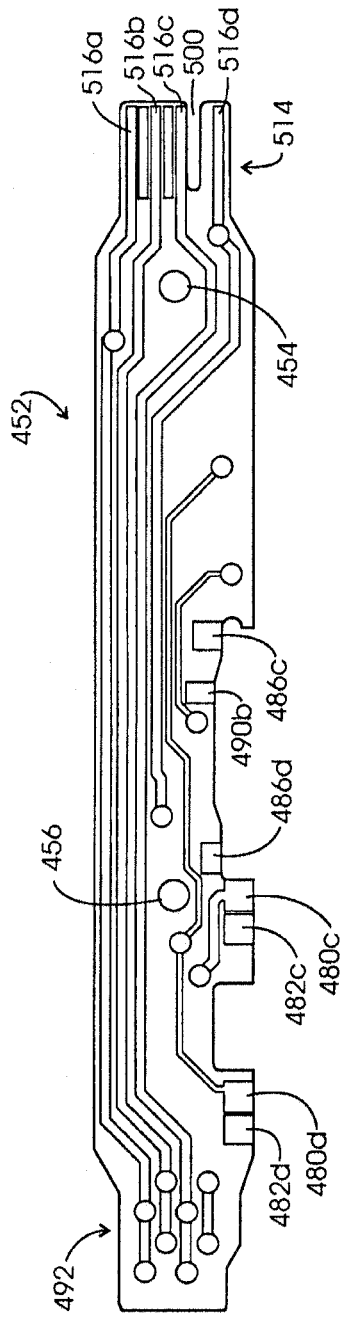

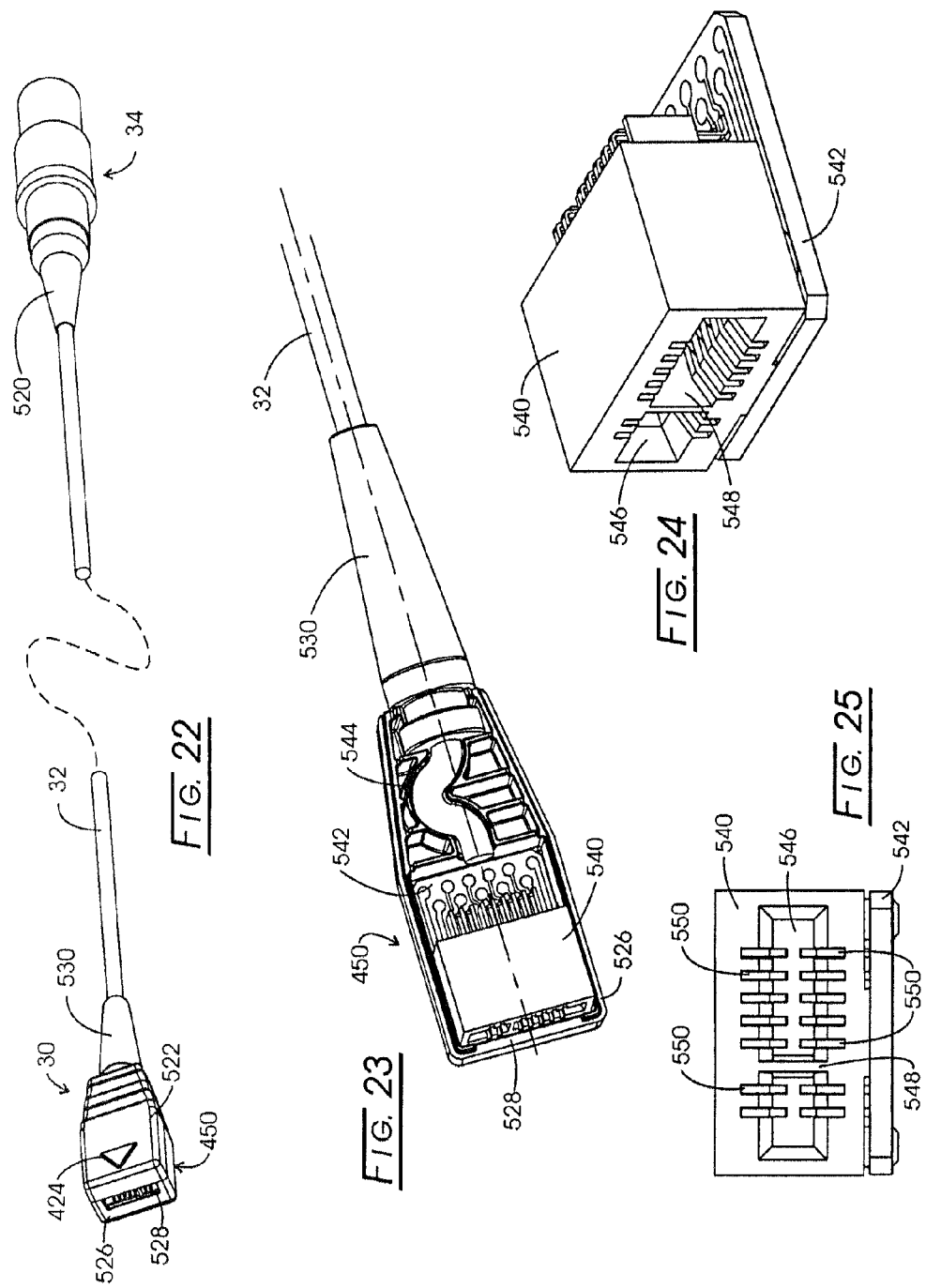

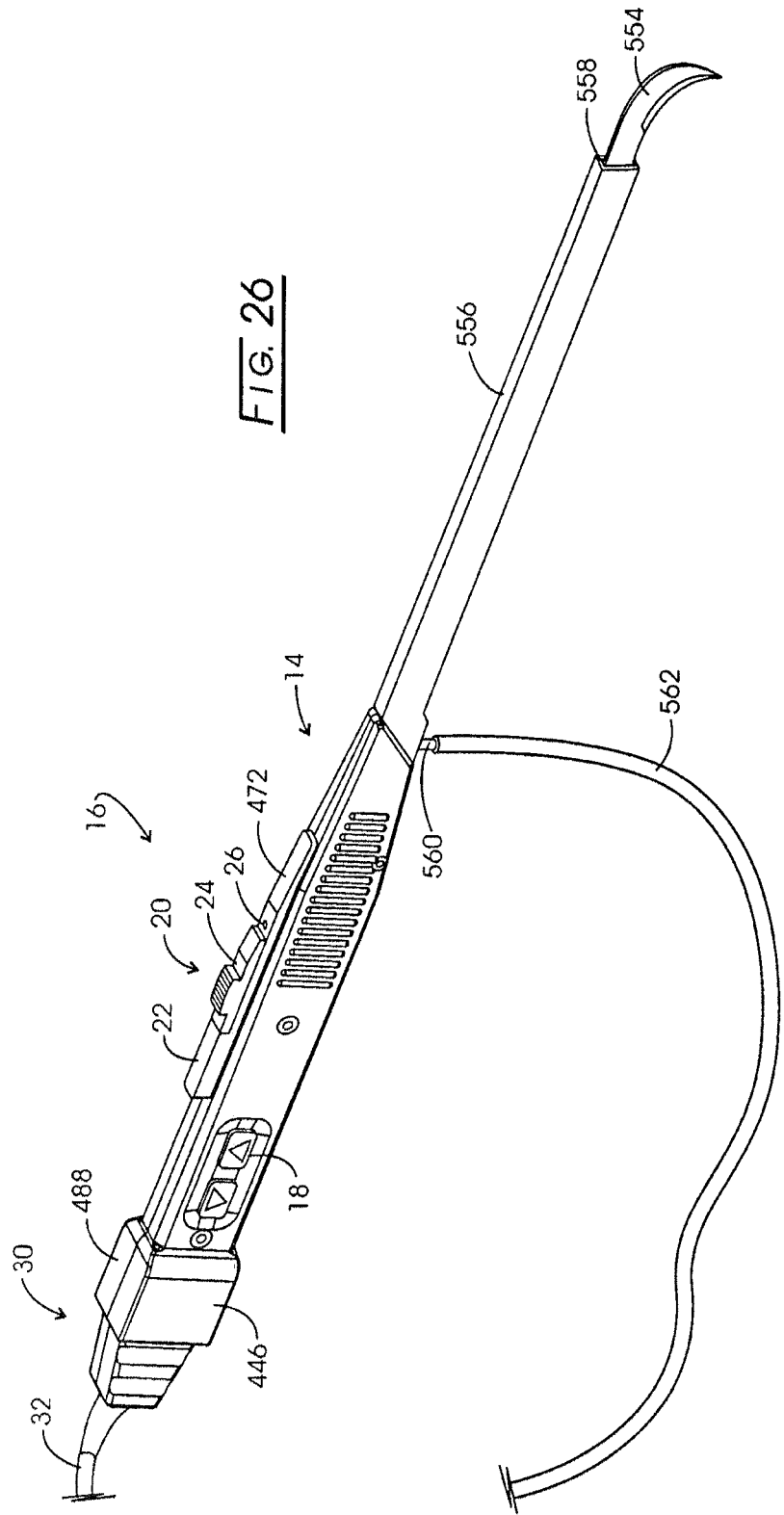

HEATED HEMOSTATIC SURGICAL BLADE SYSTEM AND METHOD

CROSS-REFERENCE TO RELATED APPLICATIONS

This application is a divisional application of U.S. application Ser. No. 11/980,310, filed Oct. 10, 2007, now U.S. Pat. No. 8,142,425, the disclosure of which is expressly incorporated herein by reference.

STATEMENT REGARDING FEDERALLY SPONSORED RESEARCH

Not applicable.

BACKGROUND

The control of bleeding during surgery accounts for a major portion of the time involved in an operation. In particular, bleeding that occurs when tissue is incised obscures the surgeon's vision, delays the operation, and reduces the precision of cutting.

One technique for minimizing the bleeding of tissue as it is being severed is known as hemostatic surgery. This technique uses a heated instrument to contact bleeding tissue. The heat is transferred from the instrument to the incised (or torn) tissue to thermally, reform collagen, thereby producing a thin collagenous film that seals over the severed blood vessels and capillaries, thereby reducing bleeding. Because heat is applied locally to tissue that contacts the heated region of the instrument, there is little tissue necrosis or damage that, if present, would retard healing.

One such hemostatic instrument is known as a hemostatic surgical scalpel. This scalpel has a sharp cutting edge similar to that of a conventional steel scalpel blade, and a heating element proximate to the cutting edge to heat the blade. During cutting, the scalpel blade is heated and the heat is transferred to the tissue being cut.

One commercial device using this technique is a hemostatic scalpel manufactured and sold by Hemostatix Medical Technology, Memphis, Tenn. and described in U.S. Pat. Nos. 3,768,482, 4,481,057, 4,485,810 and 5,308,311. This device uses a multi-segmented resistive heating element whereby the current flowing through each segment is individually controlled to maintain each segment, and hence the blade, within a narrow range of user-selected temperatures.

A drawback of previously known hemostatic heated scalpel blades has been the inability to deliver an adequate quantity of heat in close proximity to the cutting edge, to maintain a sharp durable cutting edge, and to be usable for sustained surgery under a wide variety of surgical cutting applications. Sufficient thermal delivery is critical to seal promptly the blood vessels and capillaries being severed. The quantity of heat that must be delivered increases with the rate at which the scalpel is being moved through the tissue and the degree of vascularization of the tissue. These conditions have limited the cutting rate and depth that the previously known devices can be used to hemostatically cut tissue.

Good surgical blades are commonly made of hard materials such as steels and martensitic stainless steels, but these materials generally have low thermal conductivity. High thermal conductivity materials are desirable for delivering the necessary heat, but typically do not maintain a sharp and durable cutting edge. Contact of the high thermal conductivity blades with the corrosive biological fluids and operation at elevated temperatures combine to dull the cutting edges of such blades prematurely. Moreover, they also conduct large amounts of heat to the handle of the blade, making it uncomfortable for the surgeon to hold the instrument during surgery.

Attempts to use other blade materials have been made without any apparent success, e.g., ceramic blades as described in Shaw U.S. Pat. No. 3,768,482, Johnson U.S. Pat. No. 4,219,025, Lipp U.S. Pat. No. 4,231,371, and high thermal conductivity materials treated to have hardened cutting edges as described in U.S. Pat. No. 4,770,067. These devices similarly lack the combination of desirable thermal transfer properties and a durable sharp cutting edge.

Other types of hemostatic scalpel devices having non-segmented heating elements for heating the sharp scalpel blades are described in a U.S. Pat. Nos. 4,207,896, 4,091,813 and 4,185,632. Attempts have been made to increase the delivery of heat to the tissue by using thick-film, glass-based dielectric, resistive heater and electrical lead layers printed on the metallic blade as described in U.S. Pat. No. 5,308,311. However, this approach requires heating the blade to greater than 400° C. for up to 60 minutes to melt and adhere the multiple glass dielectric lead layers. This necessary processing time at temperatures unavoidable reduces the hardness of the cutting edge due to the effect known as annealing or tempering. As a consequence of the reduced hardness, these scalpel blades cannot reach the desired level of sharpness and/or durability required for surgical procedures. In addition, the reduced level of hardness results in a more rapid rate of edge wear or dulling during the course of a surgical procedure. Furthermore, the use of thick-film, glass-based dielectric, resistive heater and electrical lead layers is not well suited to smaller blade sizes such as the well known No. 11 and No. 12 surgical blade types since the surface area required for the leads reduces the available area for the resistive heater resulting in excessive heat fluxes through the dielectric layer. Also, there is the need for scalpel blades with an extended length in order to access surgical sites such as the tonsils for tonsillectomy procedures. However, the glass-based inks are susceptible to cracking due to the long length of the blade and the associated thermal expansion mismatch between the glass-based thick-film and the blade substrate.

Also, the metallic blade as described in U.S. Pat. No. 5,308,311 utilizes an alumina dispersion strengthened copper (Glid-Cop AL 15 manufactured by Gibraltar Industries/SCM Metals Corporation, Buffalo, N.Y.) layer to provide the needed thermal conductance between the heater region and the cutting edge of the blade. As a result of the limitation of the manufactured length of alumina dispersion strengthened copper strip, the roll-bonding of this alumina dispersion strengthened copper to the cutting edge material is limited to short lengths of roll bonding and associated poor production yields. In addition, the price of the alumina dispersion strengthened copper is more than 20 times that of ordinary oxygen-free, hard copper. The prior use of dispersion strengthened copper was necessary due to the essential heat treatment of the cutting edge which involves heating the entire laminate to temperatures of over 1000° C. for more than 30 minutes. Conventional high thermal conductivity materials such as oxygen-free hard copper will become completely annealed under these heat treatment conditions making them too weak to maintain the shape and flatness of the scalpel blade.

In addition, prior art handles which support the scalpel blade have been manufactured with an integral cable. The high cost of the cable containing up to 10 or more conductors and the need for making 10 or more soldered interconnections between the cable and the handle makes the handle expensive and more susceptible to failure.

Accordingly, there is a continuing need to provide a sharp, durable scalpel blade capable of delivering sufficient thermal energy to the tissue to cause hemostasis under a wide variety of operating conditions. In addition, there is a need to simplify the complexity of the handle construction to increase its reliability and reduce the frequency of the replacement of the handle assembly.

SUMMARY

The present discourse is addressed to two designs for hemostatic surgical blades, a system within which the blades may be used, and the method for their manufacture. Thee hemostatic blades are characterized as having a symmetrical, five-layer laminar cutting portion with a cutlery grade martensitic stainless steel edge forming core which maintains an improved hardness, for instance, from 57 to 63 Rockwell C. The opposed faces of this core are roll bonded with a highly thermally conductive metal which advantageously may be a pure, oxygen-free hard copper. These oppositely disposed copper layers are each bonded with a buttressing layer, for instance, formed of austenitic stainless steel such as a type 304. The two copper layers exhibit the same thickness and the two buttressing layers exhibit the same thickness. Thus, the laminar blade is symmetrical and, notwithstanding, slight differences of thermal coefficients of expansion, the laminar component will not warp, for example, during the heat hardening of the core or in the course of curing an outwardly disposed non-stick layer.

A blade edge is formed by sharpening the martensitic stainless steel core and, by virtue of its maintained hardness, the blades can be sharpened to a higher degree of sharpness and that sharpness will be maintained during blade use for an expanded interval of such use.

Heat is supplied to the blade by a flexible substrate supported heater circuit incorporating one or more resistor segments having associated circuit leads extending to an array of blade terminals located at the end of the stem component of a blade. Two topologies for the blade circuit are described, one circuit being entirely contained at one surface of a polyimide substrate wherein the blade terminals are accessed by openings extending through the substrate. In another topology, the heater resistor segments are carried on one side of the substrate, while the lead structures extending from them are on the opposite side, communication through the substrate being provided by vias or plated through holes. For each arrangement, the flexible circuits are applied to blade blanks using a thermally conductive electrically insulating adhesive. The thus formed blades are lastly coated with a non-stick coating which is cured with a thermal dose which does not adversely affect the quality of the adhesive layer or the hardness of the core material.

One blade embodiment employs an elongate blade stem of length effective to access body cavities such as the throat. Accordingly, the instrument may be employed for tonsillectomies and the like.

The system employing the improved blades is one wherein multi-lead cables are removeably connectable with a blade-mounting handle. Thus, the cable is separately sterilizable and may have a working life span not dependent upon that of the handle. The system may employ a sleeve structure which surmounts a blade stem and may be coupled with a trap and vacuum assemblage to carry out evacuation or aspiration. Such a sleeve structure also may be employed to carry out irrigation of the surgical site, for instance, exposing unsealed blood vessels. In another system embodiment, the controller function is contained within the blade handle which, in addition to temperature adjustable up/down switches contains a temperature display and utilizes a cable which is greatly reduced in complexity, having two leads carrying d.c. current from a small converter.

Further disclosed is a method for manufacturing a hemostatic scalpel blade having a laminar portion and a stem portion which comprises the steps:

providing a core strip of cutlery grade martensitic stainless steel having a widthwise extent effective for forming the laminar portion and a thickness defined between opposite faces;

providing thermal transfer strips of a substantially pure metallic material exhibiting high thermal conductivity, having a conduction thickness and shape for bonding against each face of the core strip;

providing two buttressing strips of austenitic stainless steel having a shape corresponding with the shape of the thermal transfer strips;

roll bonding the thermal transfer strip with a face of the core strip and a buttressing strip with each thermal transfer strip to provide a symmetrical, five-layer laminar strip having a lamination thickness;

providing a stem sheet of metal exhibiting low thermal conductivity having a thickness corresponding with the lamination thickness and shape effective to form blade stem portions;

edge welding the stem sheet to the laminar strip to provide a composite sheet;

heat treating the composite sheet to an extent effective to harden the martensitic stainless steel;

cutting blade profile blanks from the composite sheet;

sharpening the martensitic stainless steel core of blanks to define a double-bevel scalpel edge;

providing heating resistor and lead circuits supported by a polymeric substrate; and bonding the circuits to blade blanks using an electrically insulative, thermally conductive adhesive.

A non stick coating may be applied over the combined blade and circuit which is oven cured at a temperature and thermal dose selected not to degrade the quality of the adhesive nor the hardness of the martensitic stainless steel core.

Other objects of the disclosure will, in part, be obvious and will, in part, appear hereinafter.

The disclosure, accordingly, comprises the apparatus, method and system possessing the construction, combination of elements, arrangement of parts and steps, which are exemplified in the following detailed description.

For a fuller understanding of the nature and objects hereof, reference should had to the following detailed description taken in connection with the accompanying drawings.

BRIEF DESCRIPTION OF THE DRAWINGS

FIG. 2 is a side view of a hemostatic scalpel blade showing the substrate mounted blade heating circuit with all copper traces on one surface of a substrate;

FIG. 3 is a side view of the hemostatic scalpel of FIG. 2 showing its opposite side;

FIG. 7 is a side view of a substrate and blade heating circuit employed with the blades shown in FIGS. 2 and 3;

FIG. 8 is a side view of the substrate shown in FIG. 7 but looking at its opposite side;

FIG. 9 is an enlarged partial view of blade heating circuit components shown in FIG. 7;

FIG. 10 is side view of another embodiment for a hemostatic scalpel utilizing a circuit carrying substrate with circuit components on both sides of the substrate;

FIG. 11 is a side view of the scalpel of FIG. 10 but showing its opposite side;

FIG. 14 is a side view showing one face of a resistor segment carrying substrate;

FIG. 15 is a side view of the circuit carrying substrate of FIG. 14 but showing its opposite side;

FIG. 16 is an enlarged view of the substrate supported resistor segment shown in FIG. 14;

FIGS. 18A-18D combine as labeled thereon to provide a flow chart describing the manufacture of surgical blades as at FIGS. 2 and 3;

FIG. 20 is a side view of one side of a printed circuit board employed with the handle of FIG. 19;

FIG. 21 is a side view of the opposite side of the circuit board shown in FIG. 20;

FIG. 22 is a broken away perspective view of a cable and associated cable connectors employed with the handle of FIG. 19;

FIG. 23 is a partial and broken away perspective view of a cable connector employed with the handle shown in FIG. 19;

FIG. 24 is a perspective view of a connector seen in FIG. 23;

FIG. 25 is a front view of the connector shown in FIG. 24;

FIG. 26 is a perspective view of a hemostatic surgical scalpel showing an elongate stem component;

DETAILED DESCRIPTION

In the discourse to follow, initially described is a blade for a hemostatic surgical instrument incorporating a martensitic stainless steel core which is surmounted by thermal transfer layers formed of copper which, in turn, are supported by austenitic stainless steel buttressing layers to provide a symmetrically disposed five-layer laminate blade. Edge welded to the blade region is a stem portion formed of a metal exhibiting a low thermal conductivity such as an austenitic stainless steel. The blade or laminate portion is heated from resistor components mounted upon a flexible substrate. Preferably, both the heater resistor components or segments and the leads extending thereto as well as terminals are provided on one singular surface of a supporting flexible substrate. This flexible circuit is bonded to blade blanks with a thermally condudtive, electrically insulative adhesive.

The next embodiment described is one wherein the flexible heater circuit resistor segments are carried on one surface of the substrate, while the leads extending therefrom are carried on the opposite side of the substrate.

The discourse then turns to the manufacturing techniques employed for the preferred embodiment. Following this discussion, the discourse looks to improvements in the scalpel handle implementation of the surgical instrument wherein the cable associated with the handle is removeable and separately autoclaveable.

Finally, an embodiment for the handle and cable is disclosed wherein essentially all control, readouts and intelligence functions of the system are contained within the scalpel handle.

Figure 1:
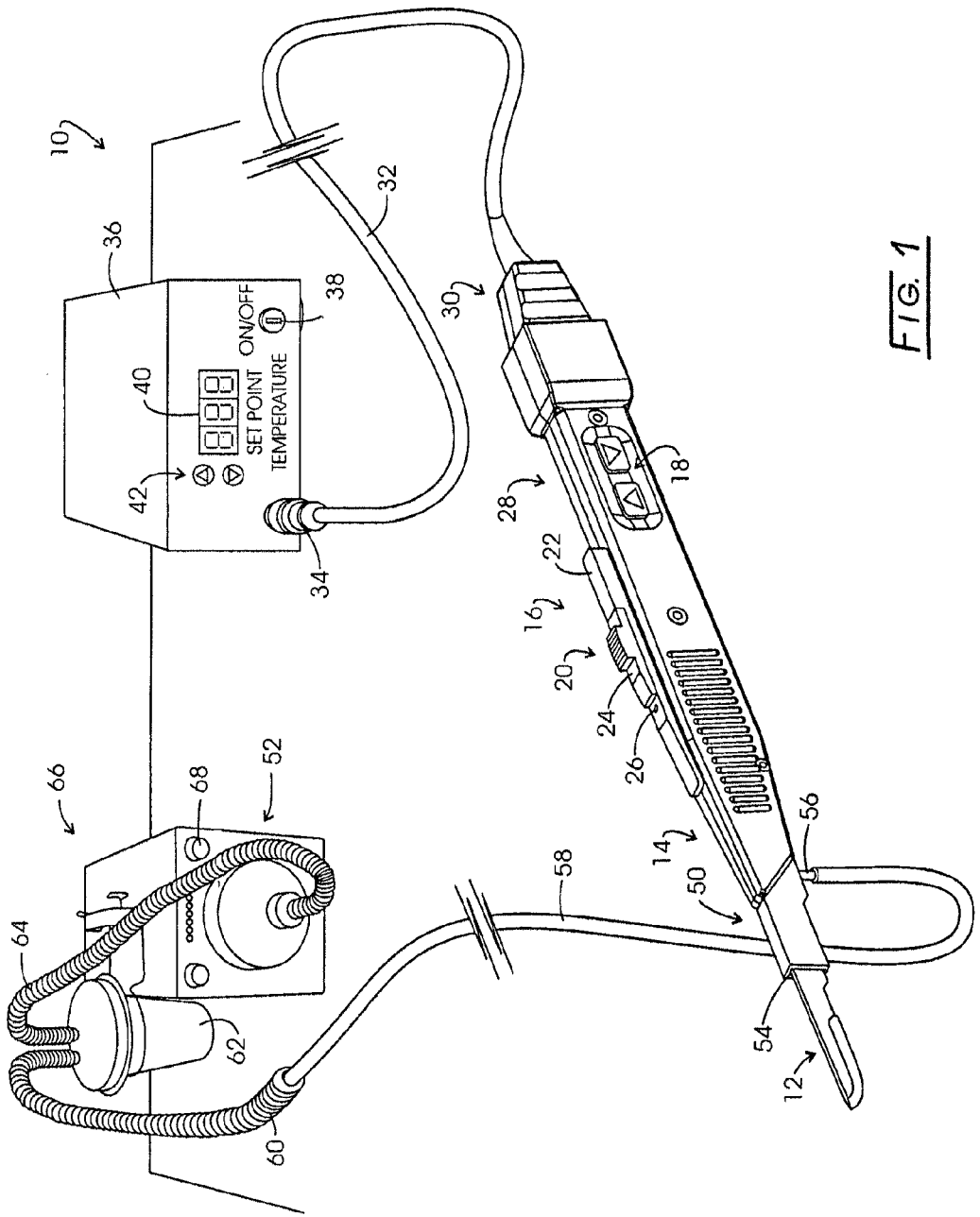
FIG. 1 is a pictorial representation of a hemostatic surgical instrument system.

Referring to FIG. 1, the system of the invention is represented in general at 10. System 10 includes a hemostatic surgical blade represented generally at 12, the stem portion of which has been mounted within the forwardly disposed engagement portion 14 of a scalpel handle represented generally at 16. Handle 16 is seen to support a temperature level adjusting up/down switch assembly represented generally at 18 and a cantilever-type operating switch represented generally at 20. Switch 20 includes two hand actuateable components, a "coag" switch component 22 which when depressed causes the blade 12 to accelerate in temperature to the highest level available, for example, 250° C. or 300° C. Forwardly of component 22 is a sliding switch component 24 shown in its closed or operating orientation such that blade 12 will be heated to that temperature elected, for example, utilizing the up/down switch assemblage 18. A small red dot 26 is revealed in this orientation to apprise the surgeon that the blade is receiving electrical energy. Sliding switch component 24 forwardly turns off the delivery of energy to blade 12 and covers dot 26.

A handle control circuit (not shown) within the handle 16 extends to a terminal assembly (not shown) located at the rearward end 28 of handle 16. That terminal assembly removeably engages a cable connector assembly represented generally at 30. The ten or more electrical leads associated with the connector assembly 30 then extends via cable 32 to a console connector 34 which is seen to be engaged within an appropriate receiving connector within the console 36 of a controller. Controller functions within the console 36 include an on/off switch 38, a set point temperature readout 40 and a temperature up/down switch assemblage represented generally at 42. Assemblage 42 carries out the same function as assemblage 18 on the handle 16.

By providing a separate cable function which is autoclaveable, its lifespan of use is not dependant upon that of handle 16. In this regard it may be observed that typically, the cost of the cable 32 is greater than that of the handle.

Returning to engagement portion 14 and blade 12, while the stem portion of blade 12 is retained mechanically and associated electrically with the control circuit of handle 16, it also is seen being associated with a thermally insulative sleeve represented generally at 50 which functions as a conduit component of an evacuation/aspiration and/or irrigation mechanism represented generally at 52. Sleeve 50 slides over the blade 12 to the orientation shown such that its forward opening constitutes an evacuation/aspiration port at 54. The sleeve is retained in position by a registration detent formed within the stem portion of blade 12. Sleeve 50 further incorporates a tubular evacuation/aspiration system connector 56 which is attached to a preferably transparent flexible polymeric tube 58. Tube 58 extends to a coupling with a flexible tube or hose of larger diametric extent shown at 60. Hose 60 extends to a fluid trap and filter assemblage 62 which is in vacuum communication via flexible hose 64 with the suction input of a suction pump assembly represented generally at 66. Vacuum or suction pump assembly 66 can be of a type marketed under the trade designation "VersaVac 2" by Stackhouse, Inc. of Palm Springs, Calif. Pump assembly 66 may be actuated into operation from a switch arrangement shown at 68.

FIGS. 2 and 3 reveal the oppositely disposed sides of a surgical blade represented generally at 74. Blade 74 is configured having a preferred topology of blade heating circuit. That circuit is seen in phantom in FIG. 2 and is formed of copper traces supported upon a thin polymeric substrate. That substrate is a 0.001 inch thick polyimide marketed under the trade designation "Kapton". The circuit includes two spiralform heater resistor segments generally located at 76 and 78 which are interconnected with four leads 80-83. Both the resistor segments 76 and 78 and the leads 80-83 are on one surface of the polyimide substrate and are formed of copper which is positioned against a thermally conductive electrically insulative adhesive. Because all of the copper trace components are on the internally disposed side of the substrate, it becomes necessary to provide access to a blade carried terminal array as represented in general at 86. That access is made by forming openings through the polyimide substrate, a procedure referred to as "skiving". Accordingly, at array 86 one observes rectangular openings providing access to leads 80-83. The outward surfaces of the blade 74 are partially coated with a liquid non-stick coating sometimes referred to as an abherent coating. This coating extends, for instance, to the dashed line 88 seen in FIG. 3. In general, the metal components of the blade 74 include a forward laminar cutting portion represented generally at 90 which includes a tip 92 and faceted cutting edge region represented generally at 94. Laminar cutting portion 90 is edge welded as represented at weld line 96 to a blade stem portion represented generally at 98. Stem portion 98 is formed of a metallic material exhibiting low thermal conductivity such as an austenitic stainless steel, for example, a type 304 stainless steel and is configured having a rearward detent 100 which is positioned for engagement with a pawl within handle 16. The stem has a thickness corresponding with that of the laminar cutting portion 90 and the non-stick coating will have a thickness within a range of from about 0.0005 inch to about 0.001 inch. Spaced forwardly of detent 100 is a registration detent 102 employed in positioning blade blanks in the process of adhesively attaching the blade heating circuit to such blanks. It may be observed in FIG. 3 that this registration detent 102 extends forwardly of the non-stick surface coating termination shown at dashed line 88 in FIG. 3. That line corresponds with the front or confronting surface of handle 16. Accordingly, detent 102 is made available for a second duty, that of securing sleeve 50 over the blade 12 (FIG. 1).

Figure 4:
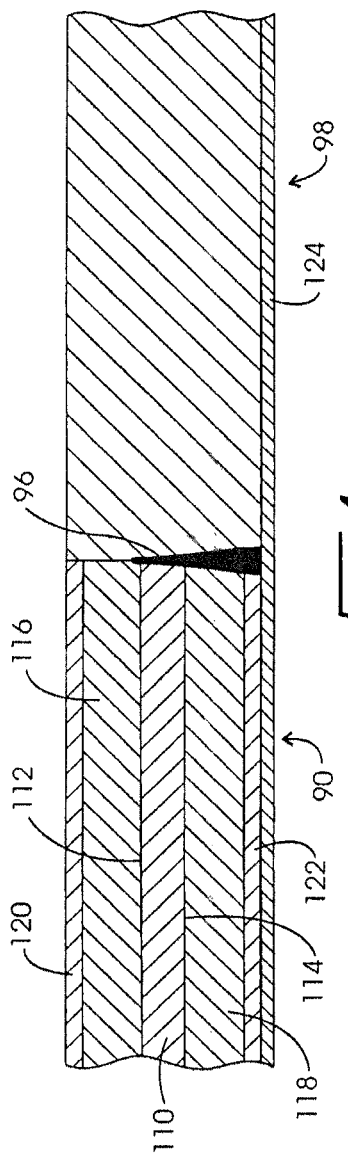
FIG. 4 is a sectional view taken through the plane of 4-4 shown in FIG. 3.

Looking to FIG. 4, a partial sectional view generally taken across the weld line 96 shows laminar cutting portion 90 structure as well as the stem portion 98 structure. Weld line 96 reappears with the same identifying numeration. Laminar cutting portion 90 is seen to be configured having a core 110 which is formed of a martensitic stainless steel with a thickness in the range from about 0.005 inch to about 0.010 inch, and preferably 0.007 inch. In general, stainless steels are iron-based alloys containing a minimum of about 10.5% chromium which forms a protective, self-healing oxide film giving them corrosion resistance. Other alloying elements are added to the steels to develop desired characteristics. In this regard, martensitic stainless steels, while being based on the addition of chromium as the major alloy element, exhibit higher carbon and generally lower chromium content. Core 110 preferably is formed with an AISI type 440C, 420C stainless steel, Hitachi Metal's stainless steel having the trade name GIN-4 or GIN-5 or Sandvik Materials Technology's stainless steel having the trade name Sandvik 13C26. The oppositely disposed faces of core 110 are seen at 112 and 114. Roll bonded to each of these faces 112 and 114 is a respective thermal transfer layer as at 116 and 118. Advantageously, layers 116 and 118 are provided as being formed of a pure, oxygen-free copper having a thickness in the range from about 0.010 inch to about 0.020 inch, and preferably 0.014 inch. To assure the integrity of layers 116 and 118, they are roll bonded with a stainless steel buttressing layer as represented respectively at 120 and 122. Stainless steel layers 120 and 122 are formed of an austenitic stainless steel. This group of stainless steels contains at least 16% chromium and 6% nickel, the basic grade 304 being referred to as 18/8. Layers 120 and 122 additionally may be formed of a precipitation hardened stainless steel, for example, type 17-7PH or 17-5PH. the layers 120 and 122 will exhibit a thickness of between about 0.062 inch and 0.004 inch.

Looking to stem region 98, note that its thickness corresponds with that of cutting region 90. Stem portion 98 may, for example, be formed of an austenitic stainless steel type 304 which exhibits a low thermal conductivity. In the figure, layer 124 represents the flexible substrate supported blade heating circuit discussed in connection with FIG. 2. The layer will accordingly incorporate copper heater and lead traces as well as a thermally conductive electrically insulative adhesive. It is important to observe in FIG. 4 that the metal laminate structure at laminar cutting region 90 is symmetrical. In this regard, the core 110 is surmounted by pure copper layers 116 and 118 of equal thickness which are, in turn, buttressed by buttressing layers 120 and 122 which additionally are of equal thickness. Accordingly, notwithstanding that the layers may exhibit slightly different thermal expansion coefficients the symmetry of the five layer laminate serves to avoid warpage because of differential expansion.

Figure 5:
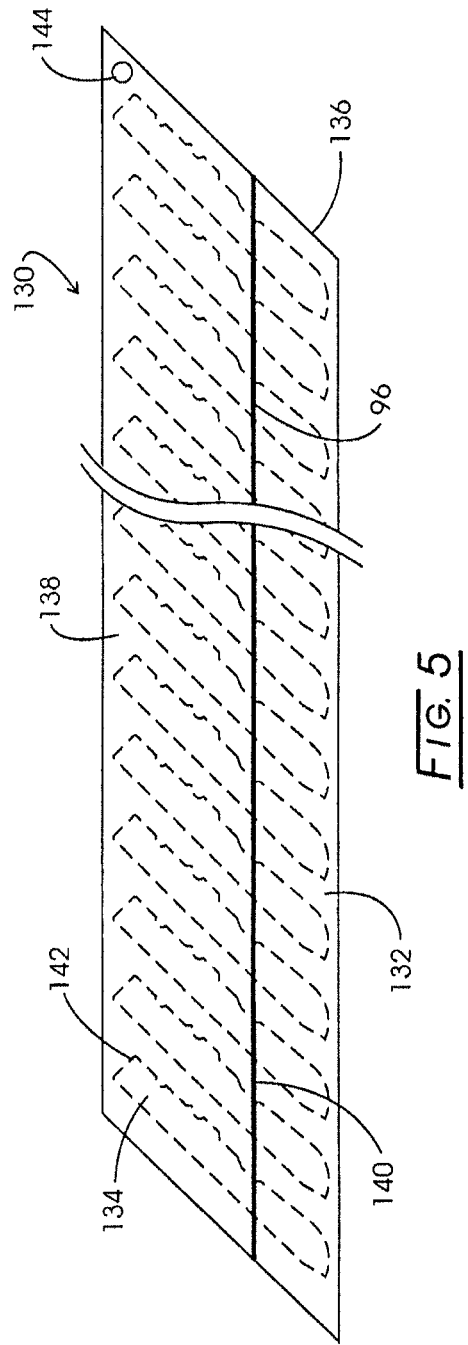
FIG. 5 is a top view of a composite sheet formed of laminar material and solid stem material as is developed during the fabrication of hemostatic scalpel blade blanks

Turning to FIG. 5, a composite sheet (dual metal laminate) represented generally at 130 is illustrated in top view fashion. Sheet 130 is shown with a slanted quadralateral periphery, the slant representing an angle of 45°. It has a nominal length of 21½ inches and is formed with a strip sheet of the above discussed symmetrical five-layer laminate which is trimmed to a desired width of, for example, 0.9 inch to about 1.2 inch. That strip is represented at 132 extending between slanted edges 134 and 136. Sheet 132 is edge welded to sheet or strip 138 which is formed, for example, of austenitic stainless steel of type 304 as discussed at stem region 98 in FIG. 4. Such edge welding of the two strips preferably is performed in long lengths (e.g., 50 feet or more) prior to cutting the dual metal assemblage into shorter (21.5 inch) strips. The edge weld line between sleeves 132 and 138 is shown at 140. Locations of blade blanks are shown in phantom extending across these sheets, certain of blade blanks being identified at 142. To accommodate the stem portions of these blanks, sheet or strip 138 will have a width of from about 1.5 inch to 2.0 inch. Where longer stem portions are contemplated, then that width would be increased substantially. To permit the composite sheet 130 to be held in a vertical orientation while being heat treated to increase the hardness of core 110, a hole 144 is drilled at the upper edge region of strip 138. Thus, warpage can be avoided during this step in the production process.

Figure 6:
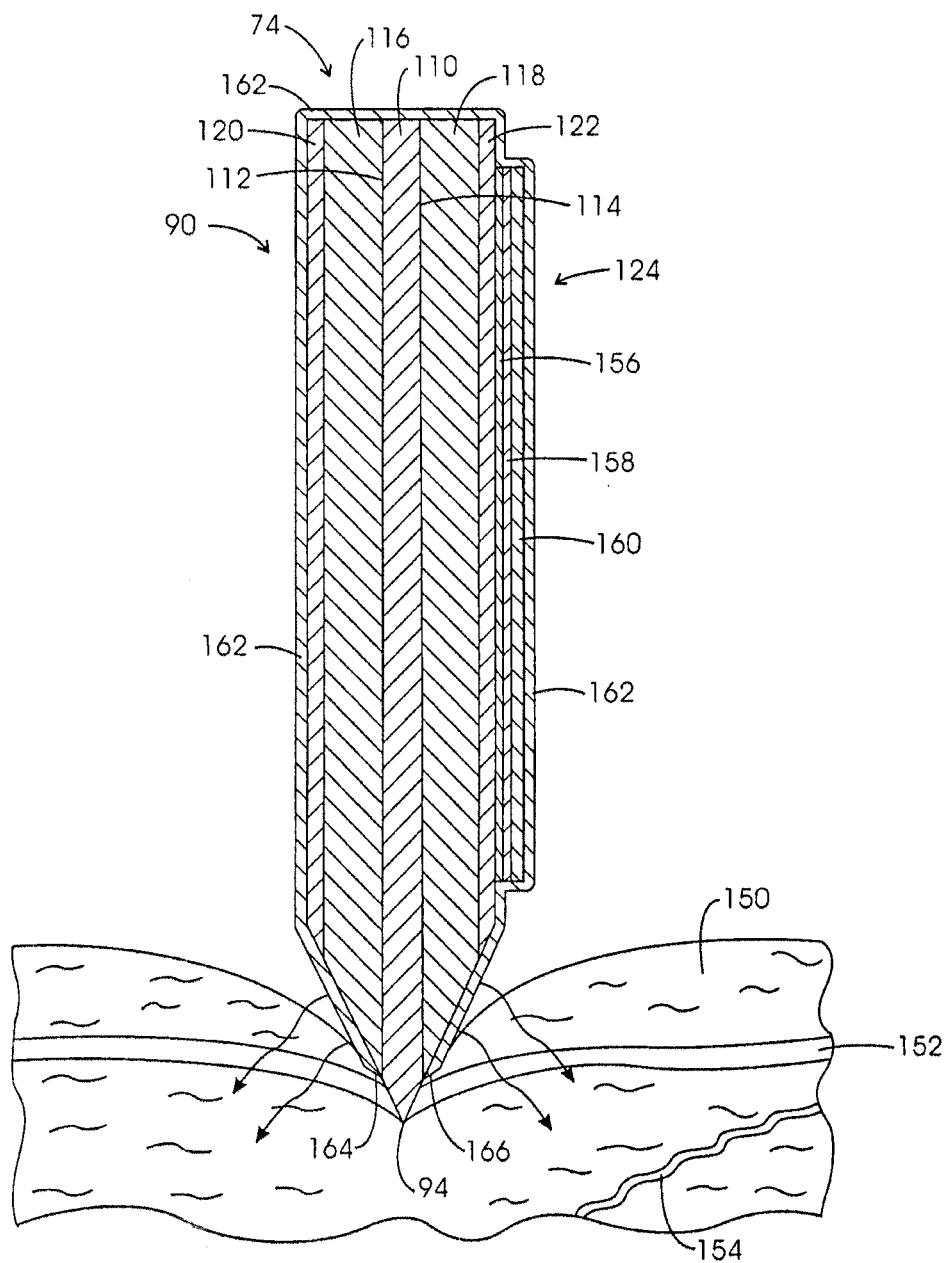
FIG. 6 is a sectional view taken through the plane of 6-6 shown in FIG. 2.

FIG. 6, in general, is a section taken through the plane is 6-6 shown in FIG. 2. Thus, it reveals a section taken through the laminar cutting portion 90 of blade 74. Accordingly, core 110 reappears in conjunction with roll bonded pure copper layers 116 and 118 which, are in turn, buttressed by roll bonded buttressing stainless steel layers 120 and 122. The layer 124 described in FIG. 4 now appears as a succession of layer material. Cutting edge 94 is seen cutting through tissue 150 which may, for instance, incorporate blood vessels as at 152 and capillaries as at 154.

Returning to multilayer heating component 124, it is seen to be comprised of a thermally conductive and electrically insulative adhesive layer 156 which is bonding the copper metallization of the substrate supported heater and lead circuit now represented at layer 158. The copper metallization 158 of this flexible circuit is supported upon a polyimide (Kapton) substrate 160 having a thickness of 0.0005 to 0.001 inch. A serpentine layer or trace of copper at 158 will have a thickness in the range from about 0.00035 inch to about 0.00070 inch. Alternatively, the metallization may be provided with other metals, such as nickel, having a temperature coefficient of resistance of at least 2000 per ° C. and a melting point greater than 350° C. Next, a nonstick layer is represented in exaggerated scale at 162. This coating 162 may, for example, be a liquid form Xylan 8585S marketed by Whitford Corporation. Such coating will have a thickness of from about 0.0005 inch to about 0.001 inch. The coating will come close to cutting edge 94, for example, coating terminations are shown at 164 and 166 located within about 0.005 inch from cutting edge 94.

FIG. 7 is a view of the inwardly disposed side of the flexible circuit including the above-described polyimide substrate 160 and the copper metallization described at 158. Two serpentine heater resistor segments again are identified at 76 and 78, that at 76 being termed a "tip" segment and that represented at 78 being termed a "heel" segment. Leads 80-83 reappear and note that the substrate 160 mimics the earlier described detents 100 and 102. FIG. 8 reveals the opposite side of this heater circuit, that side essentially being a smooth polyimide surface but note that the terminal access openings or skiving developed openings reappear with the same numeration at 86. Tip resistor segment 76 as well as heel resistor segment 78 are revealed at an enlarged scale in FIG. 9. Looking to that figure, they are shown supported by polyimide substrate 160 and portions of leads 80-83 are again identified. Of those leads, lead 83 is a power lead; lead 82 is a voltage path employed for resistance measurements to effect resistance based feedback control over the temperature of the blade; lead 81 is a central power lead providing for current flow at both the tip segment 76 and heel segment 78; and lead 80 is a power or current lead coupled with heel segment 78. In general, serpentine resistor segments 76 and 78 are made by chemical milling, photolithography or the like. Preferably, the flex circuits represented in FIGS. 7-9 are supplied with a pre-applied transfer tape adhesive located over the copper metallization.

FIGS. 10-16 illustrate another embodiment for a surgical blade. With this embodiment the blade heating circuit includes copper metallization on each side of the polyimide substrate. Recall from above that other metals may be utilized. In this regard, the leads are located on the outwardly disposed side of the substrate while the tip and heel resistor segments are located upon the opposite side. In FIGS. 10 and 11, the blade is represented in general at 170. FIG. 10 reveals in phantom a tip serpentine resistor, segment 172 and a heel serpentine resistor segment 174. These segments are in electrical communication with leads 176-179. Those leads 176-179 extend rearwardly to define a terminal array represented generally at 182. Note that leads 176-179 area on the opposite side of the polyimide substrate portions of which are seen at 184. Leads 176-179 being on the opposite side of this substrate from the resistor segments 172 and 174, plated through holes or vias 186-189 extend through the substrate 184 to permit electrical connectivity with respective leads 176-179. Because those leads are exposed with this geometry or topology, an electrically insulative cover layer represented by dashed boundary 192 is provided. Cover layer 192 terminates rearwardly at dashed termination line 194 to permit electrical exposure of the leads of array 182. As before, a substantial portion of the blade 170 is coated with a nonstick liquid coating which is cured and extends rearwardly on each side of the blade to a location represented by dashed termination line 196 seen in FIG. 11. As before, the blade 170 has a laminar cutting portion represented generally at 198 which includes a tip 200 and a faceted cutting edge region represented in general at 202. Laminar cutting portion 198 is edge welded as represented by weld line 204 to a blade stem portion represented generally at 206. Stem portion 206 is formed of an austenitic stainless steel such as type 304 which advantageously exhibits a low thermal conductivity. Stem portion 206 is configured with a rearward detent 208 located for engagement with a pawl engagement device within the handle 16. Portion 206 further incorporates a registration detent 210 which is utilized in mounting the blade heating circuit to a blade blank and extends forwardly from the front surface of handle 16. As discussed above in connection with FIG. 1, detent 210 also may be utilized to engage and retain sleeves as at 50.

An advantage of the instant blade heating circuit topology resides in the capability of forming leads 176-179 with a thicker copper metallization. For example, the copper leads may have a thickness of from about 0.0007 inch to about 0.0014 inch. As before, the thickness of the stainless steel stem portion 206 will correspond with that of laminar cutting portion 198.

Figure 12:
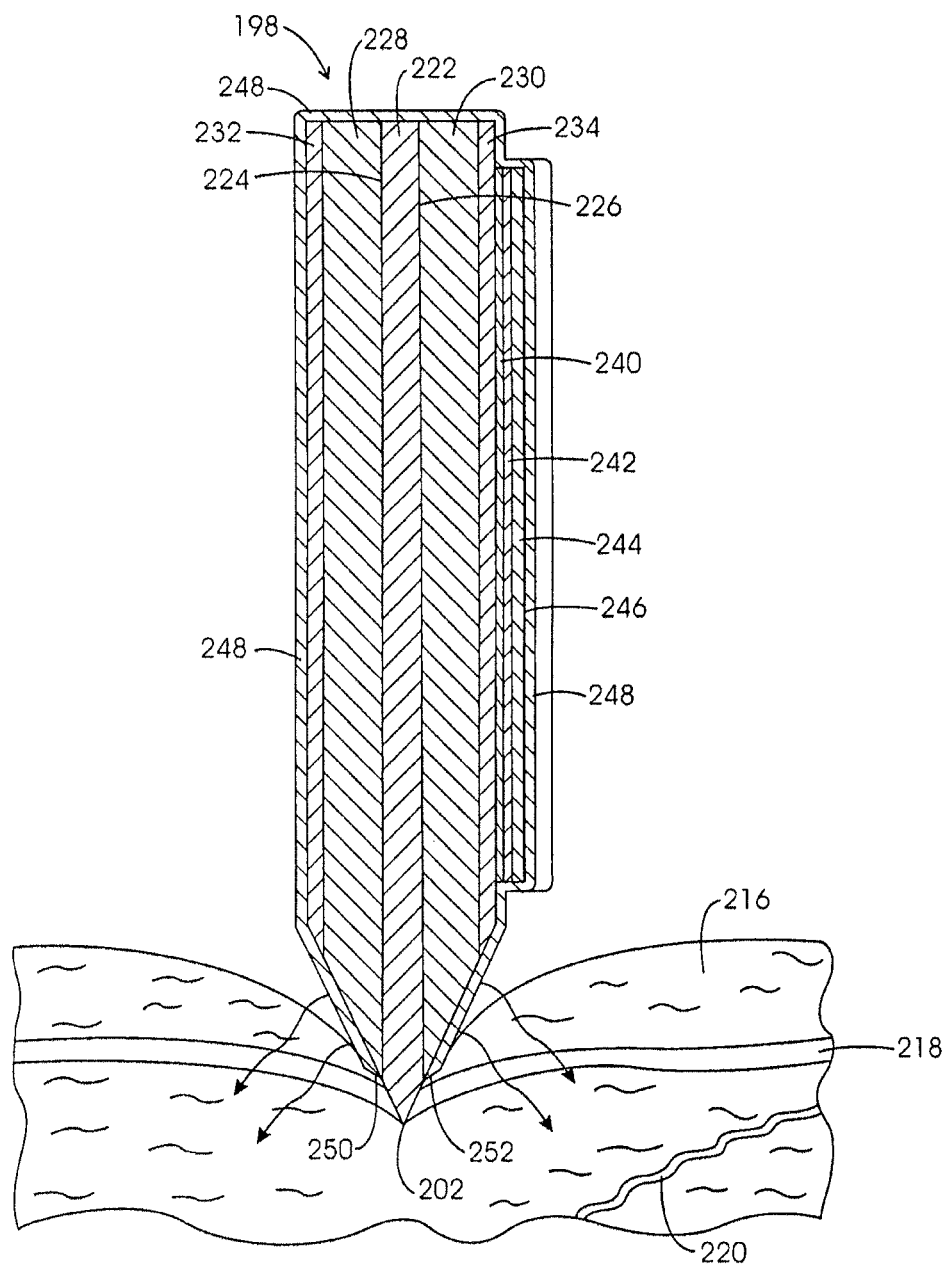
FIG. 12 is a sectional view taken through the plane 12-12 shown in FIG. 10.

Referring to FIG. 12, a sectional view taken through the plane 12-12 (FIG. 10) of the laminar cutting portion 198 of blade 170 is revealed. Cutting portion 198 is seen having cutting edge region 202 cutting through schematically illustrated tissue 216 which may includes blood vessels as at 218 and capillaries as represented at 220. Laminar portion 198 is made in the same manner as described in connection with FIG. 4. In this regard, portion 198 is configured with a centrally disposed core 222. Core 222 may be formed, for example, of a cutlery grade martensitic stainless steel as described above which will have a thickness, for example, 0.007 inch. The oppositely disposed faces of core 222 are identified at 224 and 226. These faces 224 and 226 are roll bonded with a layer of substantially pure metallic material exhibiting high thermal conductivity such as a pure or oxygen-free copper. In this regard, a copper layer is represented at 228 bonded with face 224 and a copper layer of identical thickness at 230 is bonded to core face 226. Copper layers 228 and 230 will exhibit a thickness of from about 0.010 inch to about 0.020 inch. These layers 228 and 230 are buttressed by a buttressing layer of high mechanical strength which may be present as an austenitic stainless steel having a thickness of from about 0.002 inch to about 0.004 inch. In this regard, buttressing layer 232 is shown roll bonded to copper layer 228 while buttressing layer 234 is shown roll bonded to copper layer 230.

A non-stick coating is applied over blade 170 in a manner described, for example, in conjunction with FIG. 11. In this regard, this non-stick coating is identified at 248. Coating 248 will have a thickness from about 0.0005 inch to about 0.001 inch. The coating will terminate as at terminations 250 and 252 which will come within about 0.005 inch of the cutting edge 202.

Figure 13:
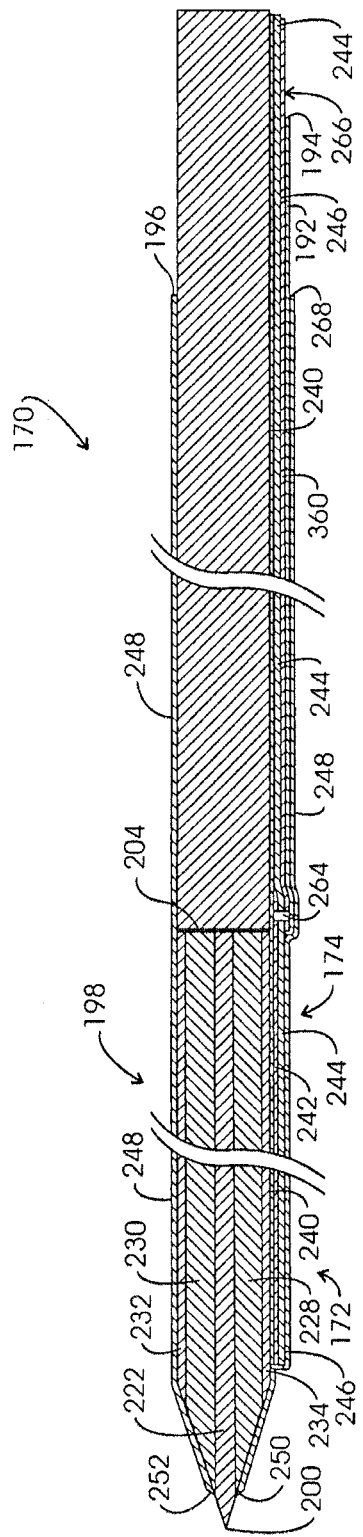
FIG. 13 is a broken away sectional of the hemostatic surgical blade of FIG. 10.

FIG. 13 is a broken away longitudinal sectional view as taken through the plane 13-13 shown in FIG. 10. In the figure, the symmetrical five-layer laminar structure is not illustrated in the interest of clarity. However, the tip 200 of laminar region 198 is identified as well as the weld line 204 connecting laminar portion 198 with blade stem portion 206. The blade heating circuit is shown to comprise a thermally conductive and electrically insulative adhesive layer 240 which extends across both the laminar cutting portion 198 and connected blade stem portion 206. The adhesive layer may, for example, be about 0.002 inch thick. Adhesive layer 240 is shown in adhesive engagement with serpentine copper resistor segments 172 and 174 as seen at 260. Those segments 172 and 174 are supported upon polyimide substrate 244, the outer surface of which again is identified at 246. Plated through holes or vias as identified in FIG. 10 at 186-189 are represented in the instant figure in general at 264 extending through substrate 244 to its outward surface 246. Surface 246 supports the four-lead array earlier described at 176-179 and now identified in general at 266. Lead array 266 is partially covered by an electrically insulative cover layer 192 which terminates at 194 to expose four terminals defined by the leads 176-179. The blade 170 is partially coated with a non-stick coating shown as a layer 248 terminating at 196 and 268.

FIG. 14 reveals the inwardly disposed side of polyimide layer 244. Vias or plated through holes 186-189 appear in electrical communication with the resistor segments 172 and 174. The remaining surface is blank with respect to the four leads which are located on the opposite side of this component. Looking to FIG. 15, the opposite side of the plated through holes or vias 186-189 are revealed in electrical communication with respective leads 176-179. Cover layer 192 and its termination 194 are represented in dashed line fashion. Note that termination 194 permits the exposure of leads 176-179 such that they may serve as terminals at that rearward location on the blade.

Referring to FIG. 16, an enlarged view of resistor segments 172 and 174 as supported from polyimide substrate 244 and electrically associated with vias 186-189 is presented. Current that feeds both the tip resistor segment 172 and heel resistor segment 174 is presented from via 188. Via 186 is associated in current transfer relationship only with tip resistor segment 172. Correspondingly, via 189 is electrically associated only with the heel resistor segment 174. Via 188 provides a shared electrical association with tip resistor segment 172 and heel resistor segment 174. Finally, via 187 represents a voltage path employed in making resistance measurements for temperature feedback control purposes.

In the process of fabricating blades as described herein, the polyimide substrate is developed in sheet form wherein a plurality of substrate components having the requisite perimeter outline are pre-formed (die cut) but retained in a single sheet. Looking to FIG. 17, a substrate sheet is represented at 280. Sheet 280 is configured to retain two rows of flexible circuit peripheral cut-outs as represented at 282a-282f and 284a-284f. The peripheral cut-outs are retained in place by cut discontinuities of very minor length, for example, as shown at 286-292 in connection with periphery 282a. In the course of fabrication, these discontinuities are readily broken. In general, in the fabrication process, metal blade blanks are accurately positioned in a fixture utilizing, for example, the earlier-described registration detents 102 and 210. The fixture will include two or more registration pins which engage registration indexing holes as are represented at 294-296 in FIG. 17. While not shown in that figure, the blade heating circuit will have been deposited upon the substrate and, preferably, over the metallization of the resistor segments there will be located a thermally conductive, electrically insulative adhesive transfer tape.

The manufacturing process for forming blades according to the preferred embodiment disclosed in connection with FIGS. 2-9 is set forth in the flow chart represented in FIGS. 18A-18D. Those figures should be considered as labeled thereon. Looking to FIG. 18A, the procedure commences with the roll bonding of three materials to form a five-layer laminate as described at block 300. Those three materials are an annealed, cutlery-grade martensitic stainless steel as represented at block 302 and arrow 304. This material exhibits a high hardness and high mechanical strength and is provided, for example, as an AISI type 440C, 420C, Hitachi Metal GIN-4 or GIN-5 or Sandvik 13C26. An important advantage of the utilization of such material as a core resides in the fact that it can be heat treated to elevate the value of its hardness. Through the utilization of an adhesive in connection with a substrate supported blade heating circuit, that hardness may retain its value throughout the fabrication process. The resulting scalpel blade edge initially will be sharper and will retain its sharpness for a longer interval of use. Another unique feature of this symmetrical five-layer laminate resides in the utilization of an annealed copper thermal transfer strip formed, for example, of an oxygen-free hard copper as identified at block 306 and arrow 308. In this regard, strips of copper of identical thickness, are roll bonded to the oppositely disposed faces of the core material. Lastly, the copper strips are supported by a buttressing layer of high mechanical strength material bonded to the outwardly disposed surfaces thereof. As before, to achieve requisite symmetry, those buttressing strips are of equal thickness. As represented at block 310 and arrow 312, the buttressing strips may be provided as an annealed austenitic stainless steel such as a type 304. The roll bonding as represented at block 300 is a process that produces a metallurgical bond as the lattice structures of the metals involved are forced into conformance with each other. High pressure, producing massive deformation of the metals, causes the sharing of electrons at the interface which produces a bond on the atomic level. No intermediate layers such as adhesives or braised metal are involved. Roll bonding services are provided, for instance, by Polymetallurgical Corporation of North Attleboro, Mass. The resultant symmetrically laminated cutting portions have been described in FIG. 5 as a strip 132. As represented at arrow 314 and block 316, this laminated five-layer strip is trimmed to a desired width. Depending upon the blade structure that width will generally be from about 0.9 inch to about 1.2 inch to provide a symmetrical five-layer thickness of about 0.047 inch to about 0.050 inch. As noted above, because of the symmetrical design in terms of materials utilized and thicknesses there is an assurance that while some differential expansion forces will be encountered, they are evenly disposed on either side of the martensitic stainless steel core.

As represented at arrow 318 and block 320, blade stem material of low thermal conductivity and appropriate strength is provided. In this regard, an austenitic type 304 stainless steel strip as described in FIG. 5 at 142 may be provided. That stainless steel strip for conventional surgical blades may be, for example, between about 1.5 inch and 2.0 inch in width and will have a thickness corresponding with the thickness of the laminar sheet 132. In general, an electron beam welding process may be employed to produce this composite sheet. The resultant weld line has been described at 96 in FIGS. 4 and 5 and the combination is described as a dual-metal laminate. Next, as represented at arrow 322 and block 324, the composite sheet or dual-metal laminate is cut into strips with a length which is suitable for electrode discharge machining. The result, as described in connection with FIG. 5 is a quadralateral with oppositely disposed widthwise sides arranged at a 45° angle and exhibiting a width, for example, of 21.5 inches. Such sloping sides have been described in FIG. 5 at 134 and 136. Additionally, as represented at arrow 326 and block 328, a hole is drilled in a corner of the type 304 stainless steel stem portion of the composite sheet for use in hanging it in a furnace in a vertical orientation during heat treatment to avoid any warpage. That hole has been described at 144 in FIG. 5.

Next, as represented at arrow 330 and block 332, the dual-metal laminate or composite sheet is heat treated such that the hardness of its martensitic stainless steel core is enhanced. As represented at block 332, this is a vacuum heat treatment to advance the hardness of that core to a Rockwell C value of about 59 to about 63. Such a vacuum furnace operates at about 1700° F. which is within about 50-70° F. of the melting point of the copper component of the laminate. Hardness is achieved with a subsequent cool down, typically, the furnace being back filled with an inert gas such as nitrogen. Through the utilization of the noted adhesive for applying the blade heating circuit this hardness is substantially maintained throughout the remainder blade forming process. With the development of such hardness, as represented at arrow 332 and block 334, blade blanks are produced. In this regard, stacks of the dual-metal laminate or composite sheets of numbers of 20 to 40 are cut within an electro-discharge machine (EDM) to develop the blanks as described, for example, at 142 in connection with FIG. 5. EDM machining is utilized to avoid cracking or damage to the hardened martinsitic stainless steel core material. During this cutting procedure, the composite sheets are retained in an oil bath. The result is a quantity of blade blanks which, as represented at arrow 340 and block 342 are cleaned and de-greased to remove residue from the electro-discharge machining process. Following such cleaning, as represented at arrow 344 and block 346, the blade blanks are sharpened with a double-bevel edge. That edge is revealed, for example, in FIG. 6 wherein the included angle extending upwardly from edge 94 is at about 28° to 30°. This relatively larger included angle contributes to assured thermal contact with involved tissue.

Figure 17:
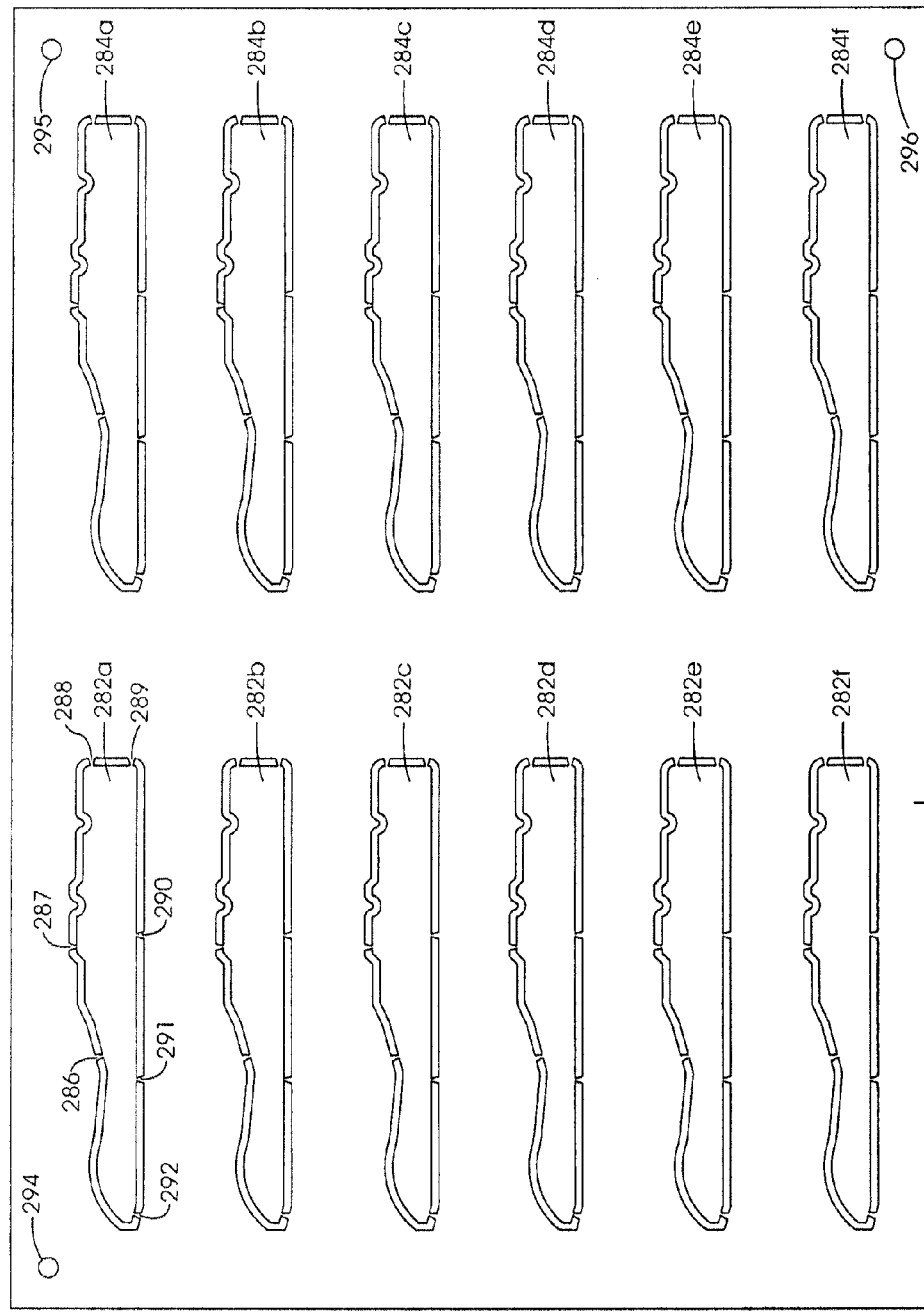
FIG. 17 is a top view of a pattern of substrate carried printed circuits as is employed in the manufacture of hemostatic surgical blades.
Figure 18B:
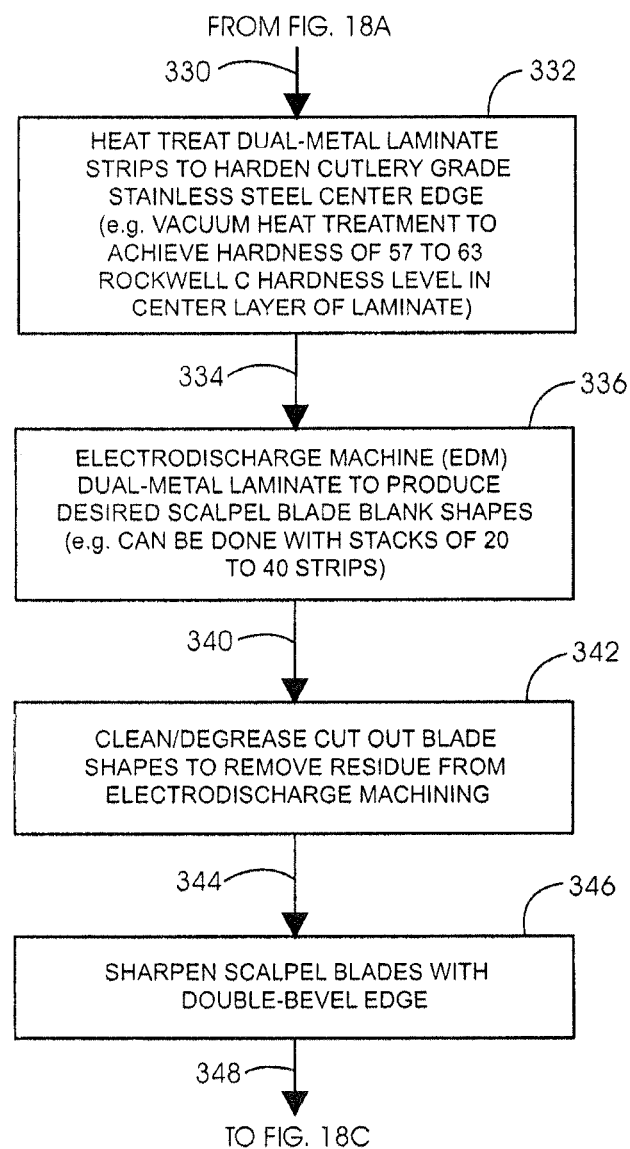

An initial blade blank test is then carried out. In this regard, as represented at arrow 348 and block 350, sharpness of the blade blanks is tested. Such testing may, for example, be provided by measuring the force required to cut through a water saturated nylon filament at three different locations along the blade edge. This test may be performed on a sampling basis for a given lot of sharpened blade blanks, for example, 5-10% of the lot. Of course, the sampling may be carried out on a 100% of lot basis. As represented at arrow 352 and block 354, a determination is made as to whether the blades have met the sharpness criteria. In the event they have not, then as represented at arrow 356 and block 358, the sharpness defective blade blanks are rejected. On the other hand, where the sharpness test has indicated the presence of satisfactory sharpened blade blanks, then as represented at arrow 360 and block 362, a substrate carrying blade heating circuit or flexible circuit is adhesively secured to the sharpened blade blanks. As noted above, to carry this procedure out, the blades are accurately positioned within a fixture or setter utilizing the forwardly disposed registration detents. The adhesive material utilized will be thermally conductive but electrically insulative. One such adhesive is a type 9882 thermally-conductive ceramic powder filled adhesive transfer tape marketed by 3-M Company of Minneapolis, Minn. This adhesive allows for an immediate joining of substrates at room temperature with light pressure. No long cure cycles at high temperatures or clamping devices are required as with thermosetting films such as epoxies. Rather than a chemical cure cycle, thermally-conductive adhesive transfer tape has a "wetting cycle" in which, on a molecular scale, the adhesive wets and interlocks surfaces instantly. The adhesive has sufficient initial tack to hold components in position and depending on the substrate, initial bond will be 20-50% of the ultimate bond strength. Such ultimate bond strength will be achieved after an extended period at ambient temperatures or several hours at elevated temperatures. The blade heater circuit as being substrate mounted (copper-on-Kapton) preferably will be supplied with the adhesive transfer tape applied thereto, a release liner being removed at the time of joining the components. Accordingly, as represented at block 364 and arrow 366, the product as described in connection with FIG. 17 is applied to the sharpened blade blank and, as represented at block 368 and arrow 370, the adhesive materials preferably will be provided as a transfer tape, the adhesive component thereof having a thickness of about 0.002 inch. Where an electrically insulated cover layer is described, for example, in connection with FIGS. 13 and 15 is utilized, it is pre-applied to the blade heating circuit lead region as discussed above at 192.

Following the adhesive bonding procedure, as represented at arrow 372 and block 374, a non-stick coating is applied to the blades, for example, by spraying, following which the cutting edge of the blade is exposed by wiping the coating off to a distance of 0.005 inch of the cutting edge. In this regard, recall the location of the coating termination identified at 164 and 166 in connection with FIG. 6 as well as at 250 and 252 in connection with FIG. 12. Supply of this non-stick coating is represented at block 376 and arrow 378. The coating identified in block 376 is a Xylan 8500 series produced by Whitford Corporation of West Chester Pa. This coating series is distinguished by its relatively low processing temperatures (275° C.) and short cure intervals. The type Xylan 8585S is formulated for good hot hardness and scratch resistance, the material containing a high temperature silicone release agent. It is important that this non-stick coating be curable at temperatures and over intervals which will not adversely effect the adhesive material described at block 368. The high thermal conductivity and electrically insulative characteristic of this material must not be adversely affected. Of course, it is important to maintain the hardness of the martensitic stainless steel core material of the blades. The use of such abherent material with associated "non-sticking" properties functions to reduce the sticking or adherent tissue, blood, coagulated blood and other biological fluids or residues (so called coagulum buildup) reduces the added thermal impedance associated with coagulum buildup. Such a coagulum buildup can reduce the hemostatic effect of an instrument. Other abherent materials which have been utilized are fluorinated polymers, fluorine-containing inorganic compounds or silicon. As described in connection with FIG. 3 at dashed line 88, the coating further is terminated towards the proximal end of the blade. That termination is also shown at dashed line 196 in FIG. 11.

Following application of the non-stick coating, as represented at arrow 380 and block 382, the non-stick coating is cured in an oven, for example, at 275° C. for five minutes in air. This curing procedure has been found not to detract from the necessary characteristics of the adhesive nor to affect the hardness of the martinsitic stainless steel core of the blades. Such combined selection of adhesive and non-stick coating with its associated curing thermal dose evolves a significant improvement over blades of the prior art.

Following curing as described in connection with block 382, two tests of the resultant blade heating circuit are carried out. As represented at arrow 390 and block 392, heater segment resistance is tested. For an associated controller to perform employing auto-calibration, that resistance, for example, should be in a range from 4.0 ohms to 6.0 ohms. Accordingly, resistance values without this range will represent an open circuit or short circuit condition. Under those conditions, the blades are rejected and 100% of the blades are put under this resistance test. Accordingly, as represented at arrow 394 and block 396, a query is made as to whether blade resistance is ok, i.e., within the noted range. Where it is not, then as represented by arrow 398 and block 400, the blade is rejected. On the other hand, where the blade passes this resistance test, then as represented at arrow 402 and block 404, a power application test is carried out to check for a weak serpentine trace with respect to the tip and heel resistor segments. In this regard, the traces may exhibit a short thinned out portion or partially cracked portion. Under a ramping-up power application such defects will cause the resistor segments to fail. Accordingly, 100% of the blades must pass this test. As represented at arrow 406 and block 408, a query is made as to whether a given blade has passed the power-up test. In the event that it has not, then as represented at arrow 410 and block 412, the blade is rejected. Where the power-up test is passed, then, as represented at arrow 414 and block 416, sterilization and packaging procedures are undertaken. Sterilization may be, for example, by gamma radiation impingement or ethylene oxide envelopment depending upon the particular adhesive utilized. Following packaging, as represented at arrow 418 and block 420, the packaged and sterilized blades are placed in finished goods inventory and, as represented at arrow 422 and block 424, ultimately the packaged blades are shipped to a customer.

It may be recalled that in connection with the discourse presented with FIG. 1, a considerable advantage is achieved by providing for the removeable insertion of cable 32 within the scalpel handle 16. Carrying multiple leads, for example, more than 10, this cable may be separately sterilized and represents a cost greater than that of the handle 16 itself. To achieve this removeable connection, the internal control circuit of the handle has been provided with a rearwardly located terminal assembly and the rearward housing components have been modified to receive and support a connector assembly. Looking to FIG. 19, the handle 16 is depicted in exploded perspective fashion. Device 16 is formed with housing defining right and left castings 430 and 432 which may be joined together by rivets 434-436 which extend through respective openings 438-440 in left casting 432 as well as respective openings 442-444 in right casting 430. Right casting 430 is configured having a rearwardly open cable connector receiver half-cavity 446. Correspondingly, left casting 432 is configured with a cable connector receiver half-cavity 448. When castings 430 and 432 are fastened together by rivets 434-436, receiver half-cavities 446 and 448 join to provide a receiving cavity which functions to support the insertion component 450 of cable connector assembly 30. Extending centrally within the handle housing is a somewhat rigid printed circuit board represented generally at 452. Circuit board 452 is retained by rivets 434 and 435 passing through respective holes 454 and 456. In this regard, the interior portions of openings 438 and 439 as well as 442 and 443 are configured with stand-offs which contact and position circuit board 452. Two such stand-offs are shown at 458 and 460 in connection with respective holes 438 and 439. Casting 430 additionally is configured having a slightly indented switch receiving region represented generally at 462 and incorporating rectangular openings 464 and 466 which are configured to receive earlier-described up/down switch assembly 18 which is identified with the same numeration in the instant figure. Castings 430 and 432 additionally are configured with one half of an upper switch opening as seen respectively at 468 and 470. The resultant upper switch opening receives a cantilevered switch identified in general in FIG. 1 at 20 and identified with the same numeration in the instant figure. Switch assembly 20 includes a somewhat elongate cantilevered sliding component with which the earlier described "coag bar" described in FIG. 1 at 22 is integrally molded. That component is identified by the same numeration in the instant figure. Formed somewhat centrally in sliding component 472 is an elongate opening 474 which receives the downwardly depending switch actuator bar 476 of earlier described sliding switch component 24. Actuator bar 476 engages and moves a gold plated switch contact slider 478. Slider 478 is configured with oppositely disposed slider contacts which in a rearward orientation engage printed circuit board 452 mounted contact pads 480a and 480b. This represents a power-on condition. However, when actuator bar 476 is slid forwardly, gold plated contact pads 482a and 482b are engaged by slider 478. This represents a power-off condition. Contact pads identical to those shown at 480a, b and 482a, b are provided on the opposite side of printed circuit board 452. integrally molded "coag" switch 22 performs in conjunction with a resilient gold plated upper contact 484, the spaced apart downwardly depending contact tines of which engage contact pads 486a and 486d as well as corresponding pads on the opposite side of printed circuit board 452. The switch is further configured with gold plated lower contact 488, the downwardly depending tines of which engage gold plated contact pad 490a mounted upon printed circuit board 452. A corresponding contact pad is mounted upon the opposite side of the printed circuit board 452. Red dot 26 reappears on elongate polymeric member 472 as was described in connection with FIG. 1. Forwardly upon printed circuit board 452 is an array of eight plated through holes represented generally at 492. These thru-holes are configured to receive and mechanically and electrically engage the inwardly depending paired tines of "tuning fork" blade contacts 494a-494d. Note that the forward end of one tine for each of these blade contacts 494a-494d is configured as a pawl intended for contacting the four rearwardly disposed lead terminals of the blades described above. The opposite tine is configured to be received in electrical isolation by a polymeric registration sleeve 496. When so received, the pawl shaped tips of these tines will engage the noted blade terminals. When a blade is received within sleeve 496 the rearwardly disposed detents described in FIGS. 2 and 3 at 100 and in FIGS. 10 and 11 at 210 will be engaged by a resilient pawl 498 retained by rivet 436. Looking to the opposite end of printed circuit board 452, note that it is formed with an internally depending keyway 500 which cooperates with connector assembly 450 to assure its proper orientation.

Figure 19:
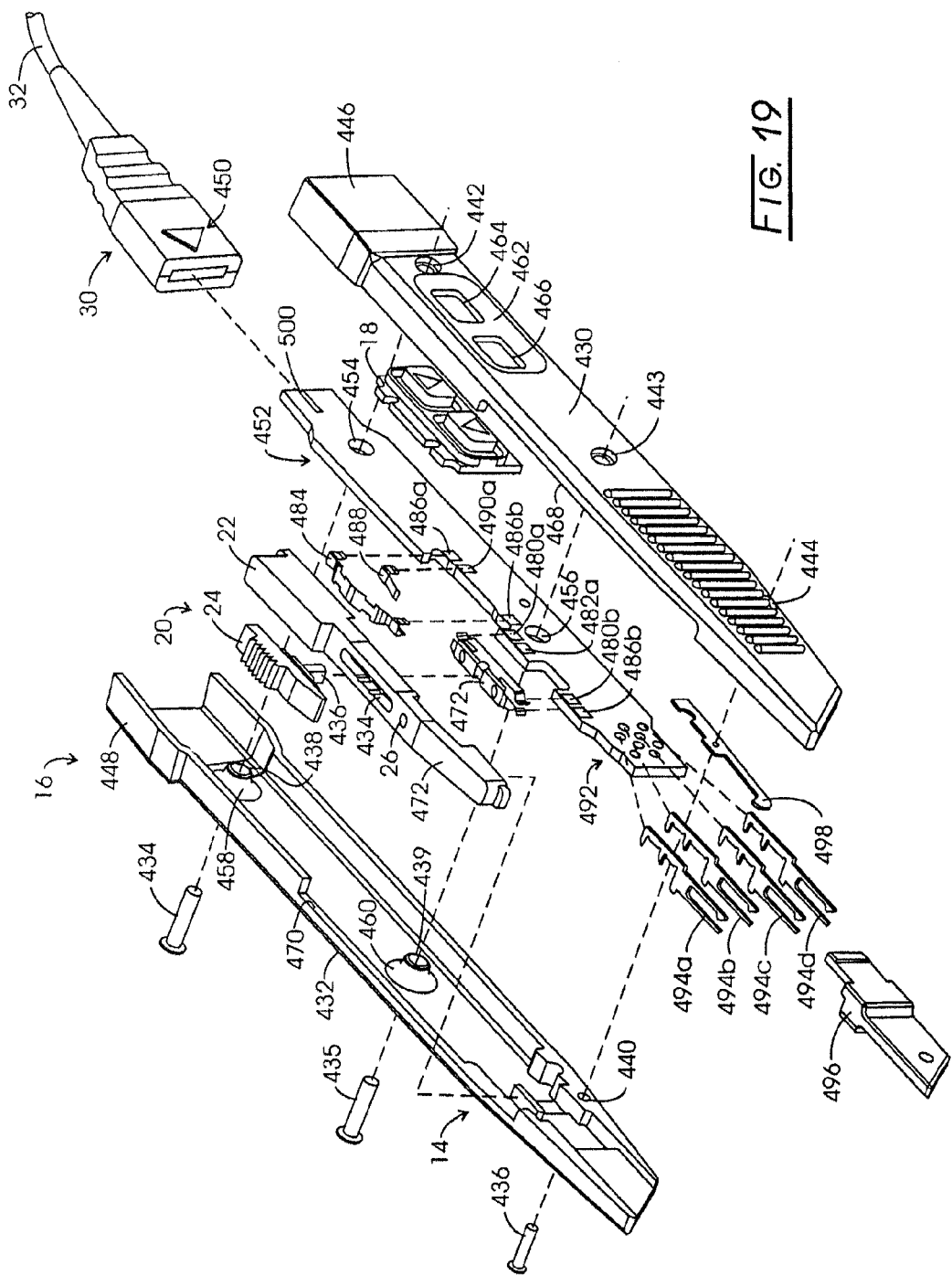
FIG. 19 is an exploded perspective view of a handle and cable connector employed in hemostatic surgery.

Referring to FIG. 20, the side of printed circuit board 452 seen in FIG. 19 is revealed at an enhanced level of detail. In the figure, holes 454 and 456 reappear as well as the plated thru-hole array 492. The dual component switch contacts for the up/down switches 18 are provided as down contacts represented generally at 510 and up contact represented generally at 512. At the rearward end of printed circuit board 452 there is a rearwardly located terminal assemblage represented generally at 514. For the side of the printed circuit board 452 shown in FIG. 20, note that there are seven terminals.

Contact pads 486a and 486b reappear in FIG. 20. The counterparts of these contact pads are shown in FIG. 21 respectively at 486c and 486d. In similar fashion, lower contact pad 490a appears in FIG. 20 and its counterpart is seen as contact 490b in FIG. 21. Forwardly of these contact pads, contact pads 480a and 480b shown in FIG. 20 have counterparts shown respectively at 480c and 480d in FIG. 21. Contact pads 482a and 482b are seen in FIG. 20 and their oppositely disposed counterparts are seen respectively at 482c and 482d in FIG. 21. In FIG. 21, the terminal array assemblage 514 is seen to incorporate four active terminals 516a-516d. These terminals extend from the blade terminals. The additional three terminals are spares.

Referring to FIG. 22, the cable 32 is represented in broken away perspective fashion. Console connector 34 reappears as a multi-pen plug with an over molded cable strain release boot 520. Connector assembly 30 is seen in perspective being formed with the upper connector back shell 522 carrying a directional arrow 524. Back shell 522 is configured for compatible mating with cable lower connector back shell 526. Within device 526 there is defined a connector opening 528. An over molded cable strain release boot is shown at 530.

Cable connector assembly 30 is configured with a commercially available cable connector. That connector is represented in FIG. 23 at 540. Connector 540 may be provided, for instance, as a type NEC1-108-02-S-D-RA1-SL, marketed by Santec, Inc., of New Albany Ind. Device 540 has 14 over and under contacts. It is shown in the figure as being electrically associated with a small printed circuit board 542 which is coupled with the plurality of leads (not shown) of cable 32. Note additionally in the figure that cable 32 is secured within an undulating channel represented generally at 544 and located rearwardly of insertion component or region 450.

Looking to FIG. 24, connector 540 is represented in perspective in combination with printed circuit board 542. That printed circuit board is configured with 14 solder pads connected, in turn, to terminals within connector socket 546. Note the registration web 548 which is received within slot 500 formed within printed circuit board 452 (FIG. 19). Looking additionally to FIG. 25, certain of the 14 terminals are identified at 550. In this regard, it may be observed that these devices are configured with 7 terminals on one side and 7on the other and that they are aligned. These terminals make contact with the 7 printed circuit board terminals at each side of printed circuit board 452 as illustrated at 514 in FIGS. 20 and 21.

As discussed in connection with FIG. 5, the austenitic stainless steel component 138 within which blade stems are formed can be increased in widthwise dimension to produce blade stems which are elongated to an extent effective for utilizing the blade component within body cavities, for example, employing a number 12 scalpel blade emulation for carrying out tonsillectomies. For this purpose, the stem portion of the blade may have a length within a range of from about 2.0 inches to about 6.0 inches. Looking to FIG. 26, handle 16 reappears with its earlier-described identifying numeration in conjunction with a number 12 scalpel blade emulation as seen at 554. Laminar blade 554 is edge welded to a blade stem portion of elongate dimension which is enclosed within a correspondingly elongate sheath or thermally insulative covering 556. As discussed in connection with FIG. 1, this sheath 556 may be configured to function as a conduit and may be secured utilizing the exposed registration detent as described at 102 in FIGS. 7 and 8 and at 210 in connection with FIGS. 10 and 11. Sleeve 556 may be formed of copper, aluminum, or stainless steel or with a biocompatible plastic such as polyimide or polyetherimide with spacing of air between the inner surface of the blade stem. Such spacing of air should define an air gap in the range of from about 0.01 to about 0.05 inches which can be developed by forming narrow ridges on the interior surfaces of the sheath. The wall thickness of the sheath 556 may range from about 0.002 inch to about 0.040 inch. Optionally, the sheath 556 may function as a conduit for evacuation/aspiration purposes. In this regard, the forward region of the sleeve as at 558 forms a port for that purpose, while rearwardly a connector tube 560 may be provided to establish a fluid path including a flexible plastic tube 562 which may be employed in the manner of tube 58 described in connection with FIG. 1. However, utilizing this evacuation/aspiration function is entirely optional.

Figure 27:
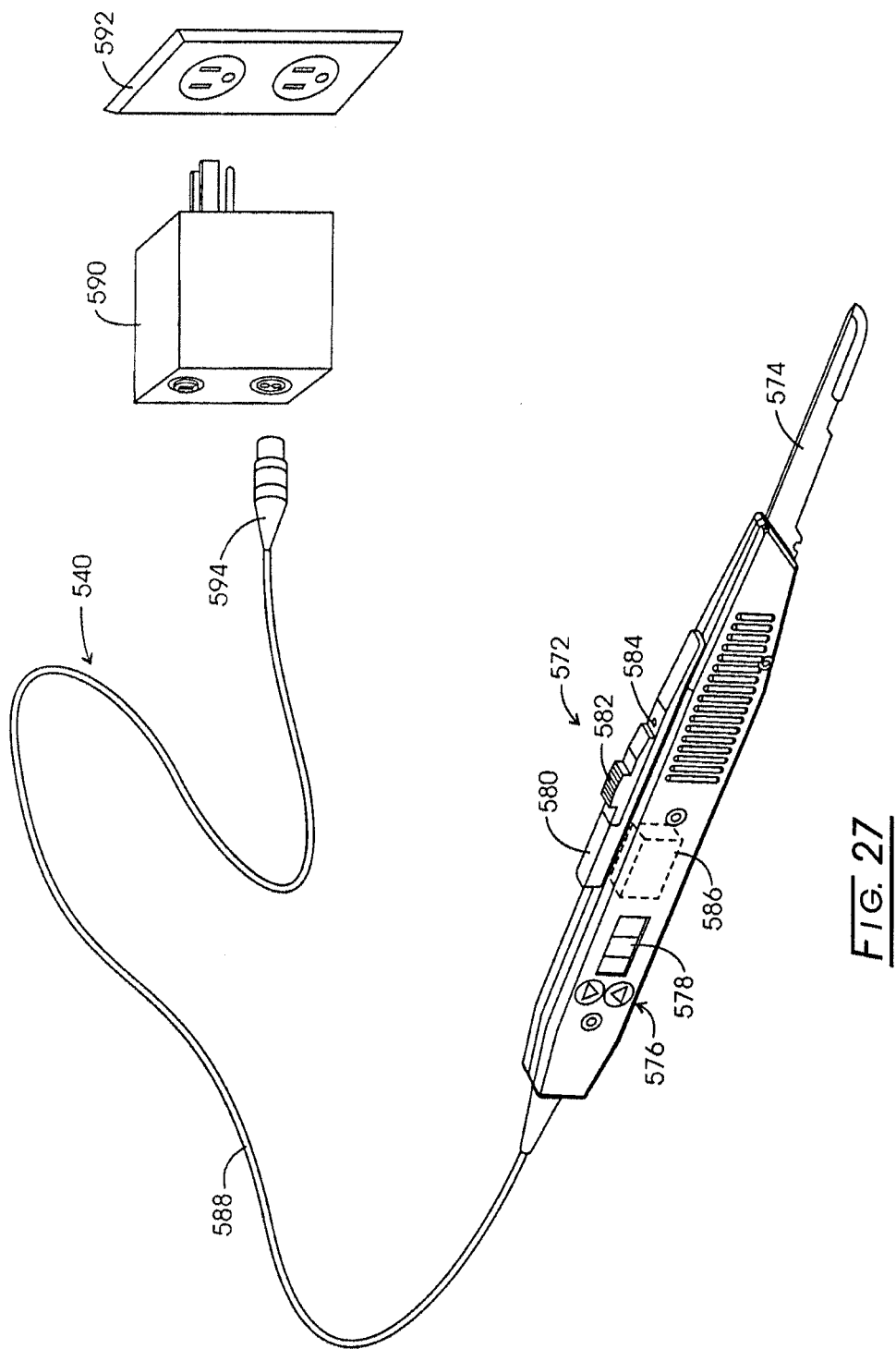
FIG. 27 is a perspective view of a hemostatic surgical system showing controller and readout functions contained within a scalpel handle.

The relatively higher cost associated with multi-lead cables as at 32 can be ameliorated by incorporating necessary electronic intelligence within the handle of the hemostatic scalpel. Such a system is represented in general at 570 in FIG. 27. In the figure, a handle is represented generally at 552 within which blade 574 fabricated as above-described, is inserted. Handle 572 incorporates up/down switches represented generally at 576 which perform in conjunction with a temperature readout display 578 which may be provided as implemented with light emitting diodes or liquid crystal components. The earlier-described coag switch is shown at 580 as well as sliding power switch 582. Switch 582 is shown in a power-on status, the red dot 584 being visible.

Note there is no controller in system 570. Controller intelligence is provided by electronics mounted within the handle 572. Such electronics is represented at dashed block 586. Because of its incorporation within handle 572, the requirements for a cable as at 588 substantially diminish. Cable 588 carries two electrical leads which assert d.c. current to handle 572. That d.c. current is developed from a small d.c. source 590 which, in turn, is powered from a conventional wall outlet 592. Connection to the source 590 is with a relatively simple two part plug 594, the opposite end of cable 588 being hard wired within handle 572.

Figure 28:
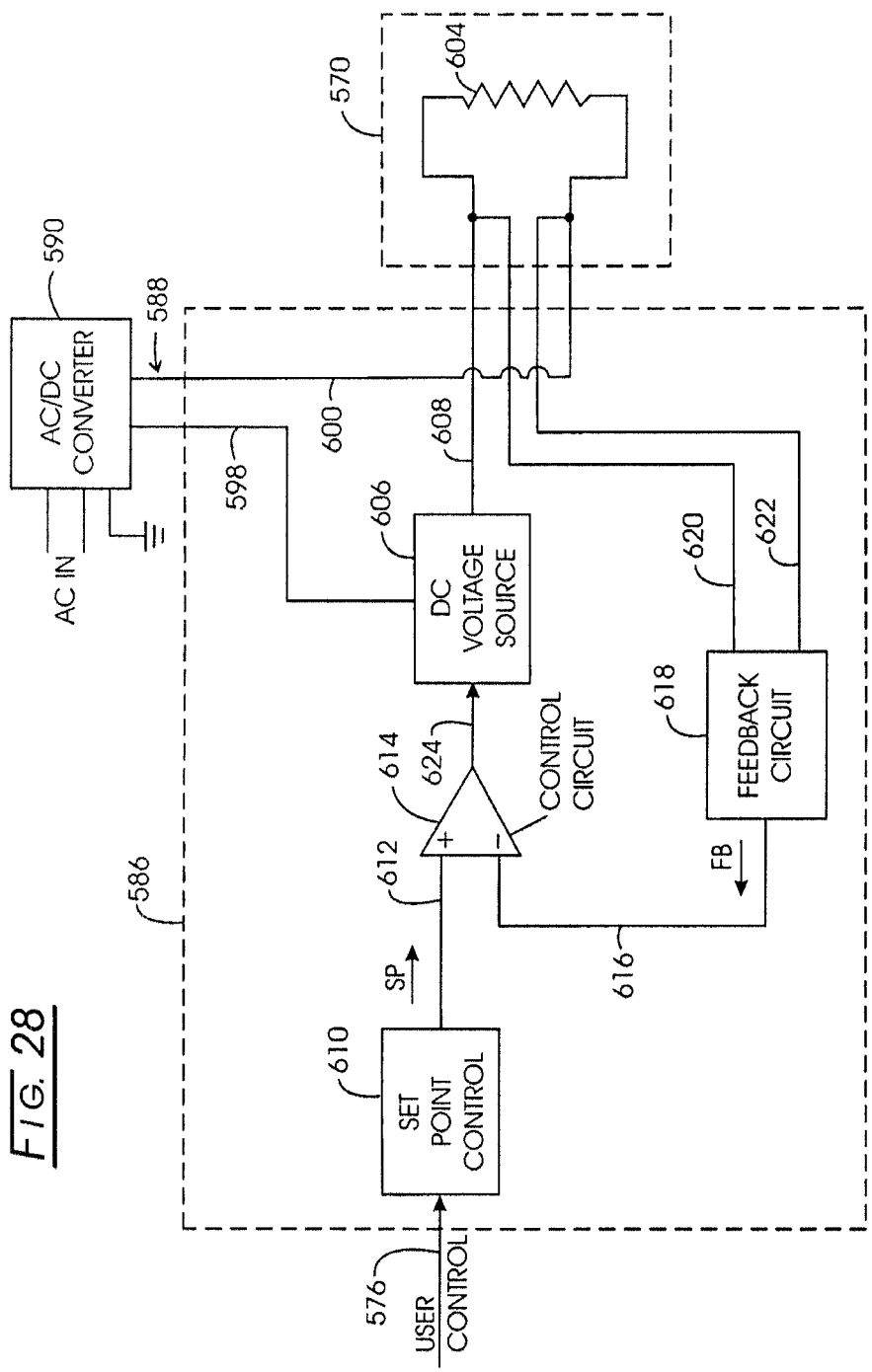
FIG. 28 is a schematic diagram of a control circuit which may be employed with the handle of FIG. 27.

Referring to FIG. 28, a simplified schematic representation of the control feature 586 is set forth. In the figure, the two leads carrying d.c. current via cable 588 are shown at 598 and 600. A hemostatic scalpel blade is represented at dashed boundary 574 with a symbolic heater resistor segment 604 driveably coupled from a d.c. voltage source 606 via line 608 and further being coupled with cable lead 600. User control as evolved from the up/down switches 576 is represented with the same numeration in conjunction with an arrow extending to a set point control function represented at block 610. Control 610 provides a set point signal as represented at line 612 to a comparing function represented symbolically at 614. The opposite input to comparison function 614 is from line 616 and a feedback circuit 618. Circuit 618, in turn, as represented at lines 620 and 622 derives a voltage tap from lines 608 and 600 to develop a temperature related signal at line 616. A resultant correction signal then is developed from comparing function 614 at line 624 to correspondingly adjust d.c. voltage source 606 and regulate the temperature at resistor segment 604.

Since certain changes may be made to the above apparatus, system and method without departing from the scope of the disclosure herein involved, it is intended that all matter contained in the descriptions hereof or shown in the accompanying drawing shall be interpreted as illustrative and not in a limiting sense.

The invention claimed is:
1. A hemostatic surgical system, comprising:
 a hemostatic surgical blade with a laminar cutting portion having a cutting edge carrying core of martensitic steel, oppositely disposed layers of thermally conductive metal structurally supported by austenitic steel buttress- ing layers, a blade stem portion formed of metallic material exhibiting low thermal conductivity fixed in supporting relationship with the laminar cutting portion, and a blade heating circuit having leads extending from a blade terminal assembly to one or more resistor heater components in thermal exchange relationship with a said buttressing layer and layer of thermally conductive metal;

a scalpel handle having a forwardly disposed engagement portion configured to removably receive and mechanically support said blade at said stem portion, a handle control circuit having an electrical contact assemblage engagable with the blade terminal assembly and extending in electrical engagement with a rearwardly located terminal assembled; and a cable having a forward end coupled with a handle receiving cable connector assembly removably engagable with said handle and said rearwardly located terminal assembly and said cable having a rearward end configured for receiving electrical energy from a source.

2. The system of claim 1 further comprising:

a fluid conduit supported at said scalpel handle with a port located adjacent said surgical blade laminar cutting portion and extending to a source of vacuum and/or irrigation fluid.

3. The system of claim 1 in which:

said blade stem portion is formed having a length effective to surgically access tissue within a body cavity; and further comprising a thermally insulative sleeve surmounting at least a portion of said blade stem portion.

4. The system of claim 3 in which:

said sleeve is configured as a component of a fluid conduit having a port located adjacent said surgical blade laminar cutting portion and coupled in fluid transfer relationship with tubing supported at said handle and extending to a source of vacuum and/for irrigation fluid.

5. The system of claim 1 in which:

said handle control circuit further comprises:

a resistor heater temperature adjusting switching assembly and a controller responsive thereto, and further responsive to derive resistance related temperature values to provide temperature control and coupled with said cable connector assembly to receive a d.c, power input at said rearwardly located terminal assembly.

6. The blade of claim 1 in which:

said blade heating circuit comprises an electrically insulative polymeric substrate supporting a circuit defining metallic trace pattern and bonded to said blade stem portion and laminar cutting portion.

7. The blade of claim 6 in which:

said blade heating circuit is bonded to said blade stem portion and laminar cutting portion with an electrically insulative, thermally conductive adhesive.

8. The blade of claim 7 in which:

said circuit defining metallic trace pattern is entirely supported upon one surface of said polymeric substrate.

9. The blade of claim 8 in which:

said blade heating circuit blade terminal assembly is accessible through one or more openings extending through said substrate, from a surface opposite said one surface.

10. The blade of claim 6 in which:

said polymeric substrate is formed of a polyimide; and said circuit defining metallic trace pattern is formed of copper.

11. The method of manufacturing a hemostatic scalpel blade having a laminar portion and a stem portion, comprising the steps:

providing a core strip of cutlery grade martensitic stainless steel having a widthwise extent effective for forming the laminar portion and a thickness defined between opposite faces;

providing thermal transfer strips of a substantially pure metallic material exhibiting high thermal conductivity, having a conduction thickness and shape for bonding against each face of the core strip;

providing two buttressing strips of austenitic stainless steel having a shape corresponding with the shape of the thermal transfer strips;

roll bonding a thermal transfer strip with a said face of the core strip and a buttressing strip with each thermal transfer strip to provide a symmetrical, five-layer laminar strip having a lamination thickness;

providing a stem sheet of metal exhibiting low thermal conductivity having a thickness corresponding with said lamination thickness and shape effective to form blade stem portions;

edge welding the stem sheet to the laminar strip to provide a composite sheet;

heat treating the composite sheet to an extent effective to harden the martensitic stainless steel;

cutting blade profile blanks from the composite sheet;

sharpening the martensitic stainless steel core of blanks to define a double-bevel scalpel edge;

providing heating resistor and lead circuits supported by a polymeric substrate; and bonding the circuits to blade blanks using an electrically insulative, thermally conductive adhesive.

12. The method of claim 11 further comprising the step:

applying a non-stick coating over the combined blade and circuit; and oven curing the applied non-stick coating.

13. The method of claim 12 in which:

said non-stick coating is cured at a temperature of about 275° over a short interval of time defining a thermal dose; and said electrically insulative thermally conductive adhesive is selected to maintain its performance characteristics after having been subjected to said thermal dose.

14. The method of claim 11 in which:

said thermal transfer strips are provided as strips of oxygen-free hard copper.

15. The method of claim 11 in which:

said heat treating is a vacuum heating carried out to an extent effective to harden the martensitic stainless steel core to a Rockwell C hardness of from about 50 to about 63.

16. The method of claim 11 in which:

said heating resistor and lead circuit is provided as a copper trace pattern supported upon a flexible polyimide substrate.

17. The method of claim 11 in which:

said bonding step is carried out by;

arranging a plurality of blade blanks on a fixture in a predetermined pattern;

providing a plurality of said circuits supported by the substrate with the perimeters partially out and exhibiting a circuit pattern corresponding with the predetermined blade blank pattern; and positioning the circuit pattern upon and in registry with the blade blank pattern in conjunction with the location of said adhesive.

* * * * *